(12) United States Patent  
Cordes et al.

(10) Patent No.: US 7,837,691 B2
(45) Date of Patent: Nov. 23, 2010

(54) DYNAMIC KNEE BALANCER WITH OPPOSING ADJUSTMENT MECHANISM

(75) Inventors: Kevin Cordes, Orangevale, CA (US); Michael G. Fisher, Folsom, CA (US)

(73) Assignee: Synvasive Technology, Inc., Reno, NV (US)

( * ) Notice: Subject to any disclaimer, the term of this patent is extended or adjusted under 35 U.S.C. 154(b) by 1473 days.

(21) Appl. No.: 11/149,944

(22) Filed: Jun. 9, 2005

(65) Prior Publication Data

US 2005/0267485 A1 Dec. 1, 2005

Related U.S. Application Data

(63) Continuation-in-part of application No. 10/773,608, filed on Feb. 6, 2004, now Pat. No. 7,442,196.

(51) Int. Cl.
*A61B 17/58* (2006.01)
(52) U.S. Cl. ...................................................... 606/88
(58) Field of Classification Search ............. 606/86–88; 623/20.14–20.36
See application file for complete search history.

(56) References Cited

U.S. PATENT DOCUMENTS

| 4,211,228 | A | 7/1980 | Cloutier |
| 4,220,146 | A | 9/1980 | Cloutier |
| 4,501,266 | A | 2/1985 | McDaniel |
| 4,524,766 | A | 6/1985 | Petersen |
| 4,567,886 | A | 2/1986 | Petersen |
| 5,163,949 | A | 11/1992 | Bonutti |

(Continued)

FOREIGN PATENT DOCUMENTS

EP 1 402 857 3/2004

(Continued)

OTHER PUBLICATIONS

Delio, "Hoping for a Knee-Jerk Reaction" Wired News. 2004.,[retrieved on Aug. 22, 2005]. Retrieved from the Internet on <URL: http://wiredvig.wired.com/news/medtech/0,1286,62716,00.html?tw=newsletter_to>.

(Continued)

*Primary Examiner*—Eduardo C Robert
*Assistant Examiner*—Mary Hoffman
(74) *Attorney, Agent, or Firm*—Townsend and Townsend and Crew LLP

(57) ABSTRACT

A device for performing a surgical procedure on a knee comprises a femoral assembly comprising a stationary femoral member attachable to the distal femur, an adjustable femoral member movably coupled with the stationary member to adjust tension in at least one ligament of or adjacent the knee and an adjustment mechanism coupled to the assembly. The adjustable member includes at least one positioning feature that moves relative to the distal femur as the adjustable member is adjusted and identifies at least one position on the distal femur. The adjustable member is movably couplable with a tibial member engaged with a proximal tibia to allow the knee to be moved through a range of motion without removing the femoral and tibial members. The mechanism includes an actuator positioned proximate a medial or lateral portion of the adjustable member. The actuator is configured to adjust an opposite portion of the adjustable member.

60 Claims, 32 Drawing Sheets

U.S. PATENT DOCUMENTS

| | | | |
|---|---|---|---|
| 5,197,488 | A | 3/1993 | Kovacevic |
| 5,207,711 | A | 5/1993 | Caspari et al. |
| 5,360,016 | A | 11/1994 | Kovacevic |
| 5,464,406 | A | 11/1995 | Ritter et al. |
| 5,470,354 | A | 11/1995 | Hershberger et al. |
| 5,489,311 | A | 2/1996 | Cipolletti |
| 5,514,183 | A | 5/1996 | Epstein et al. |
| 5,520,695 | A | 5/1996 | Luckman |
| 5,540,696 | A | 7/1996 | Booth, Jr. et al. |
| 5,597,379 | A | 1/1997 | Haines et al. |
| 5,630,820 | A | 5/1997 | Todd |
| 5,649,929 | A | 7/1997 | Callaway |
| 5,656,785 | A | 8/1997 | Trainor |
| 5,669,914 | A | 9/1997 | Eckhoff |
| 5,688,282 | A | 11/1997 | Baron et al. |
| 5,733,292 | A | 3/1998 | Gustilo et al. |
| 5,735,904 | A | 4/1998 | Pappas |
| 5,782,925 | A | 7/1998 | Collazo et al. |
| 5,800,438 | A | 9/1998 | Tuke et al. |
| 5,860,980 | A | 1/1999 | Axelson, Jr. et al. |
| 5,880,976 | A | 3/1999 | DiGioia, III |
| 5,911,723 | A | 6/1999 | Ashby et al. |
| 6,022,377 | A | 2/2000 | Nuelle et al. |
| 6,056,756 | A | 5/2000 | Eng et al. |
| 6,096,043 | A | 8/2000 | Techiera et al. |
| 6,488,711 | B1 | 12/2002 | Grafinger |
| 6,575,980 | B1 | 6/2003 | Robie et al. |
| 6,632,225 | B2 | 10/2003 | Sanford et al. |
| 6,648,896 | B2 | 11/2003 | Overes et al. |
| 6,972,039 | B2 | 12/2005 | Metzger et al. |
| 6,984,249 | B2 | 1/2006 | Keller |
| 7,097,662 | B2 | 8/2006 | Evans, III et al. |
| 2003/0130665 | A1 | 7/2003 | Pinczewski et al. |
| 2003/0187452 | A1 | 10/2003 | Smith et al. |
| 2004/0019382 | A1 | 1/2004 | Amirouche |
| 2004/0064073 | A1 | 4/2004 | Heldreth |
| 2004/0064191 | A1 | 4/2004 | Wasielewski |
| 2004/0236424 | A1 | 11/2004 | Berez et al. |
| 2005/0010302 | A1 | 1/2005 | Dietz et al. |
| 2005/0119661 | A1 | 6/2005 | Hodgson et al. |
| 2006/0081063 | A1 | 4/2006 | Neubauer et al. |
| 2006/0241640 | A1 | 10/2006 | Briard et al. |
| 2007/0198022 | A1 | 8/2007 | Lang et al. |

FOREIGN PATENT DOCUMENTS

| | | | |
|---|---|---|---|
| WO | WO 97/09939 | A1 | 3/1997 |

OTHER PUBLICATIONS

Eckhoff et al., "Three-Dimensional Morphology and Kinematics of the Distal Part of the Femur Viewed in Virtual Reality", *Jnl. Bone & Jt. Surg.*, vol. 85-A Supplement 4, 2003, 97-104.

Howe et al., "Robotics for Surgery," *Annu. Rev. Biomed. Eng.* 1999, 01:211-240.

Mihalko et al., "Comparison of Ligament-Balancing Techniques During Total Knee Arthroplasty," *Jnl. Bone & Jt. Surg.*, vol. 85-A Supplement 4, 2003, 132-135.

Palmer et al., "Total Knee Arthoplasty"[online],[retrieved on Dec. 11, 2003]. Retrieved on from the Internet <URL: http://www.emedicine.com/orthoped/topic347.htm.> (18 pages total).

Rapp, "Electronic Knee Implant May Benefit Future TKR Patients" *Orthopedics Today*, vol. 25, No. 3; (Mar. 2005), p. 14-15.

Ries et al., "Soft-Tissue Balance in Revision Total Knee Arthroplasty," *Jnl. Bone & Jt. Surg.*, vol. 85-A Supplement 4, 2003, 38-42.

Ries et al., "Soft-Tissue Balance in Revision Total Knee Arthroplasty," *Jnl. Bone & Jt. Surg.*, vol. 86-A Supplement 1, 2003, 82-86.

The Gray Sheet, "Knee Implant Surgery Techniques Can Obscure Tech Advances—NIH Panel", FDC Reports *"The Gray Sheet"*, Dec. 15, 2003, p. 11.

The Gray Sheet, "Knee Implant Wear Debris, Changing Demographics Weighed by NIH Panel", FDC Reports *"The Gray Sheet"*, Dec. 1, 2003, p. 10.

The Gray Sheet, "NIH Consensus: More Knee Replacements Among Young, Old to Grow Market", FDC Reports *"The Gray Sheet"*, Dec. 15, 2003, p. 12.

"Achieve Dynamic Balance" flier distributed at Feb. 23-27, 2005 Annual Meeting of American Academy of Orthopedic Surgeons in Washington, DC. by Synvasive Technology Inc.

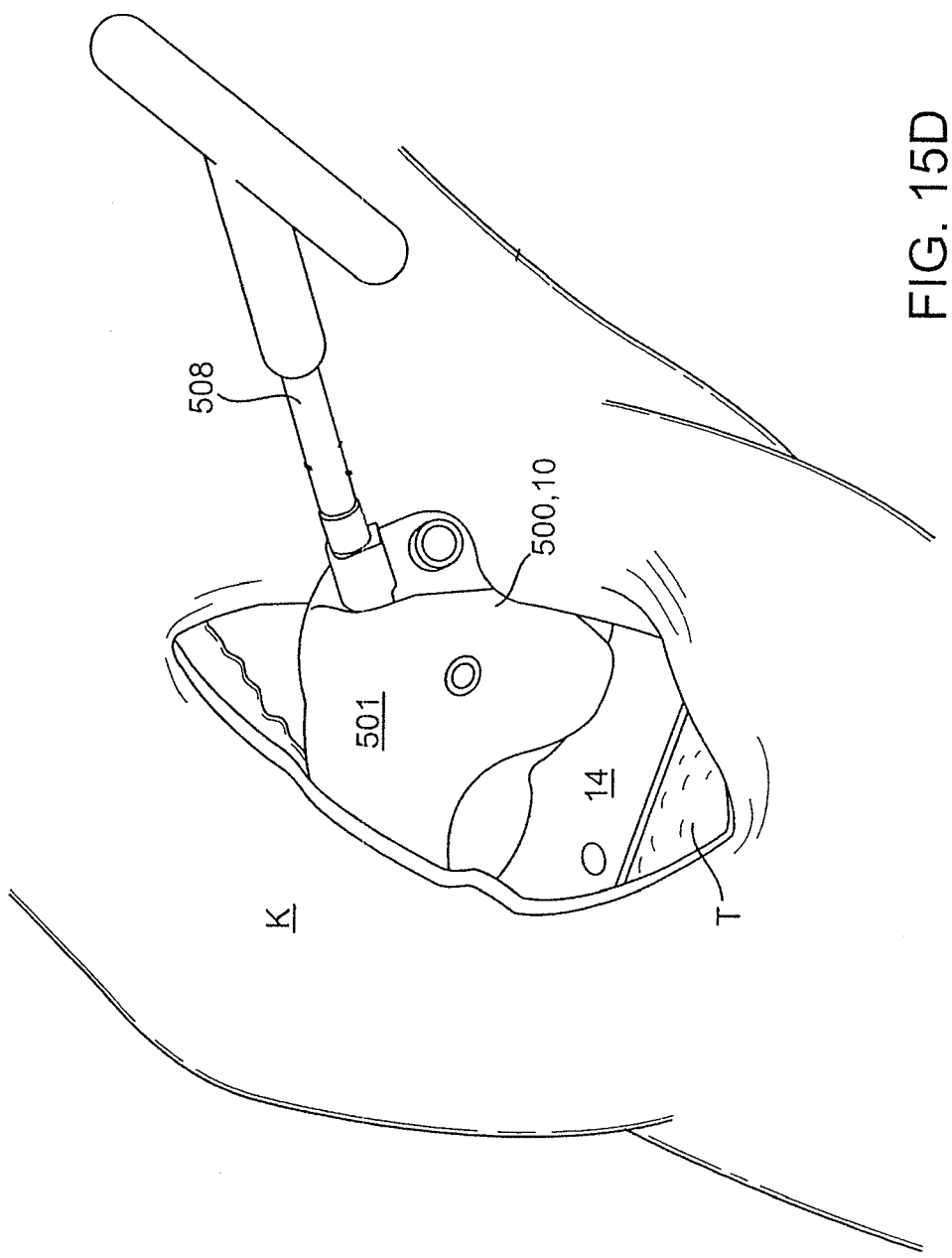

DYNAMIC KNEE BALANCER WITH OPPOSING ADJUSTMENT MECHANISM

CROSS-REFERENCES TO RELATED APPLICATIONS

The present application is a continuation-in-part of U.S. patent application Ser. No. 10/773,608, filed Feb. 6, 2004, the full disclosure of which is hereby incorporated by reference. The present application is also a continuation-in-part of U.S. patent application Ser. No. 10/973,936, filed Oct. 25, 2004, the full disclosure of which is hereby incorporated by reference.

FIELD OF THE INVENTION

Embodiments of the invention relates to medical/surgical devices, systems and methods. More specifically, embodiments of the invention relate to devices, systems and methods for enhancing a knee surgery procedure.

Total knee replacement surgery, also referred to as total knee arthroplasty ("TKA"), is becoming an increasingly important treatment for chronic knee pain and joint dysfunction. It is estimated that approximately 400,000 TKA surgeries are performed annually in the U.S. for end-stage knee arthritis. Advances have been made in TKA surgical devices and techniques, including a drive toward minimally invasive TKA surgeries. Minimally invasive TKA surgeries include smaller incision sizes and often leave the patella non-everted during surgery, in hopes of less trauma to the patient and quicker recovery times. It is estimated that approximately 10% of all TKA surgeries in the U.S. are now being performed minimally invasively. If advances in Minimally Invasive TKA continue to be made, the procedure may become more readily available to younger patients, obese patients, and the like, who may need TKA but who do not fall within in the "ideal" age range traditionally defined as between 60 and 75 years old. Improved techniques and devices would also mean enhanced outcomes for all TKA patients, with better functioning of the knee joint and longer useful life of the prosthetic knee.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

One of the greatest challenges in TKA surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may track improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Balancing ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc, during knee flexion. In addition, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. To complicate the matter further, minimally invasive TKA incisions are smaller than incisions typically made in "open" TKA surgeries. Additionally, the incision made during minimally invasive TKA surgery is biased to the medial side, leaving the lateral side of specifically the distal femur "closed" to access of front or end loaded surgical instruments Rather than or in addition to ligament release, the components of a total knee prosthesis may be selected and positioned to balance ligament tension. Since the femoral and tibial components of the prosthesis are attached to cut surfaces of the distal femur and proximal tibia respectively, placement and orientation of the bone cuts are also important. Typically, the tibial component of the prosthesis is positioned on a flat, horizontal cut surface of the proximal tibia (at a 90 degree angle relative to the long axis of the tibia), and the position and orientation of the tibial component typically do not vary greatly from knee to knee. However, by making a cut on the tibia at 90 degrees to the long axis of the same, a bigger space is created laterally than medially, due to the tibia's natural varus slope, which has been offset by the "classic" cut of 90 degrees. Most of the variation in positioning of the total knee prosthesis typically occurs in positioning the femoral component and the femoral bone cuts. The surgeon attempts to make these femoral bone cuts to achieve a position and orientation of the femoral prosthetic component so as to optimally balance ligament tension through a full range of motion of the knee. As with ligament release however, it is often very challenging to position the femoral bone cuts and femoral prosthetic component to provide ideal ligament tension through the range of motion. This is due primarily to the complexity of motion about the knee, as described above, and the difficulty of placing the femoral component so as to maintain desired ligament tension through the full range of motion. Proper balancing is further complicated by minimally invasive exposures as the surgeon is only afforded a partial line of sight. Irrespective of the newfound surgical difficulties experienced with minimally invasive TKA, the rotational, proximal/distal and anterior/posterior orientations and locations of the femoral component are all critical for duplicating the kinematics of the knee.

In a typical TKA procedure, multiple cuts are made to the distal femur before attaching the femoral component of the prosthesis. Most procedures, for example, involve making a distal cut across the distal end of the femur, anterior and posterior cuts, and angled anterior and posterior chamfer cuts to help secure the femoral component solidly in place. In order to effectively and accurately make these resections, orthopedic surgeons typically use a cutting block or cutting guide, used to guide a surgical saw blade or rotary tool, which is temporarily attached to the distal end of the femur. Positioning of such a cutting block, therefore, is crucial to forming well-positioned bone cuts for attachment of the femoral prosthetic component.

A number of devices and techniques have been described that attempt to facilitate ligament balancing during a TKA procedure. Some techniques, such as those described in U.S. Pat. No. 5,733,292, involve trial prosthesis components which are used after femoral and tibial bone cuts are made to assess ligament tension. Some devices, such as those described in U.S. Patent Application Publication No. 2003/0187452, are used to measure a gap between the distal femur and proximal tibia in extension and to help a surgeon recreate that same gap when the knee is in flexion. Other "gap checking" devices are described in U.S. Pat. No. 6,575,980. Other devices have been developed to help measure an amount of ligament tension or to apply a desired amount of tension to the ligaments. U.S. Pat. No. 4,501,266, for example, describes a knee distraction device for applying a desired amount of tension. Many paddle-like devices have been suggested for applying or measuring tension across a knee joint, such as the devices described in U.S. Pat. Nos. 5,597,379; 5,540,696; 5,800,438; 5,860,980; 5,911,723; and 6,022,377.

One proposed alternative to the cutting block technique for making bone cuts on a distal femur involves the use of robotic surgical systems for making distal femoral bone cuts. With robotic surgery and surgical navigation, a surgical saw blade or bur is still used, but the bone cuts are positioned as a result of fiducial-based or shape-based registration of the patient's anatomy. In fiducial-based approaches, fiducials, or markers are attached to pertinent anatomical structures prior to imaging. During surgery, the markers are exposed, and a sensor system conveys their location to the computer. A wide variety of sensing systems available, including optical trackers, electromagnetic transceivers, articulated probe arms, and ultrasonic and laser range finders. In shape-based approaches, the shapes of anatomical structures are fitted to preoperative image data. The patient measurements can be obtained from a variety of sensing techniques, including tracing curves, scanning distances, or processing images, via one or some of the aforementioned sensing systems. One description of the use of robotic surgery systems in knee surgery procedures is found in Howe, R D, and Matsuoka, Y, "Robotics for Surgery," Annu. Rev. Biomed. Eng. 1999, 01:211-240.

Although some of the devices and techniques described above have helped enhance and facilitate TKA procedures, currently available devices and techniques still have a number of shortcomings. Most importantly, currently available devices do not allow a physician to adjust ligament tension in a knee and also receive positional information based on that adjustment that can be used to facilitate completion of the TKA surgery. For example, many currently available devices are applied only in extension or only in flexion of the knee, or must be removed and replaced when the knee is moved from extension to flexion. Thus, it is difficult or impossible to assess ligament tension through the full range of motion using many currently available devices. Some devices rely on measuring a gap or amount of tension in extension and then recreating the gap or tension in flexion. Again, this does not always result in collateral ligament balance throughout the range of motion of the knee. Still other devices are very cumbersome and/or complex. Many include large parts which fit external to the knee joint and necessitate the patella being moved to the side during measurement or other phases of the TKA procedure. Furthermore, current devices typically do not reside primarily within the joint space during a surgical procedure to allow for the natural movements, rotations and translations of the tibia and femur as the knee is flexed through a range of motion. Additionally, current devices are not designed for minimally invasive exposures, not allowing balancing/adjustment of specifically the lateral side, which is not accessible due to the medially-biased incision and non-everted patella.

Although robotic surgery may provide a level of improvement over more traditional techniques, it is typically difficult or impossible using current robotic techniques to dynamically mark or register and sense the proper dynamic position to make well-positioned, subsequent bone cuts for attachment of the femoral prosthetic component. Thus, even with robotic systems, it is still challenging to achieve a desired ligament balance to enhance knee stability, range of motion and patellar tracking. These and other shortcomings of currently available devices and methods continue to make ligament balancing, and specifically ligament balancing in minimally invasive TKA surgeries, one of the most challenging aspects of TKA surgery.

Therefore, a need exists for improved devices, systems and methods for enhancing TKA surgery and specifically for dynamically balancing ligaments during minimally invasive TKA to improve range of motion, stability, and patellar tracking of the prosthetic knee joint. Ideally, such devices would help a surgeon balance ligaments dynamically, through a full range of motion of the knee, allowing for the natural rotation of the tibia and the natural translation of the femur while the tibia is being flexed about it. Also ideally, such devices and methods would allow a surgeon to achieve a desired ligament tension balance before committing to and making final bone cuts to the femur. Such devices would also ideally be simple to use in conjunction with cutting guides, saw blades or burs, and robotic and navigational systems, preferably allowing the patella to remain in place during assessment of ligament tension. At least some of these objectives will be met by the present invention.

BRIEF SUMMARY OF THE INVENTION

Embodiments of the invention provide devices, systems and methods for enhancing knee surgery procedures, and more specifically total knee replacement procedures (total knee arthroplasty, "TKA"). Various embodiments provide a device including a femoral assembly that includes a stationary femoral member for removably attaching to a distal femur and an adjustable femoral member coupled with the stationary member for providing adjustability. The adjustable member is movably couplable with a tibial member engaged with the proximal tibia of the knee, allowing for the natural movements, rotations and translations of the tibia and femur to take place as the knee is flexed and/or extended through a range of motion, resulting in dynamic ligament tension balancing through a range of motion of the knee.

The adjustable femoral member is adjustable to adjust tension in at least one ligament of or adjacent the knee. The adjustable member can be adjusted either on the lateral or medial side. Typically, the adjustable member is adjustable on the lateral side by an adjustment mechanism that includes an actuator such as an adjustment screw disposed on the medial side of the adjustable member/femoral assembly. This and related configurations allow adjustments to be made without everting the patella (or performing another procedure) to gain access to the surgical sites at the distal femur and/or proximal tibia. When the adjustable femoral member is adjusted to adjust ligament tension, one or more positioning features of the adjustable member can be used to provide positioning information to help position and/or orient a cutting guide, surgical saw blade, bur, mill, surgical navigation system, robotic surgical system or the like. This positioning information can then be used to make subsequent bone cuts to the distal femur, or to otherwise mill or shape the distal femur, so that when a femoral prosthetic component is fitted, the knee has one or more of a desired stability, range of motion and/or patellar tracking. Various embodiments of the invention thus help to dynamically balance ligament tension in a knee during minimally invasive TKA surgery and to do so without requiring eversion of the patella tendon or other surgical procedure. This reduces procedural time, incision size and rehabilitation time for the patient while providing for improved surgical outcome in terms of having a dynamically balanced knee. Specific performance improvements include one or more of range of motion, stability or patella tracking vs. the unbalanced knee.

For purposes of the present description, the terms "ligaments of the knee," "ligaments in the knee," "ligaments adjacent the knee," and the like are all synonymous and all refer generally to any ligaments within the knee joint space, around the knee, adjacent the knee, or near the knee. These terms typically refer to the ligaments that assist in the functioning of the knee, and often the ligaments referred to are the medial collateral ligament, the lateral collateral ligament, the anterior cruciate ligament and the posterior cruciate ligament. Although the following description focuses on the use of various embodiments of the invention in TKA surgical procedures, these and/or other embodiments may be adapted for use with other orthopedic surgical procedures known in the art. Such procedures can include without limitation, other knee surgical procedures, other joint surgical procedures (e.g., hip replacement, or repair of laxity in the knee, shoulder, elbow or other joint) or other orthopedic surgical procedures.

One embodiment of the invention provides a device for performing a surgical procedure on the knee comprising at least one stationary femoral member for removably attaching to a distal femur and at least one adjustable femoral member movably coupled with the stationary member to adjust tension in at least one ligament of or adjacent the knee. The adjustable femoral member includes at least one positioning feature that moves relative to the distal femur as the adjustable femoral member is adjusted and thus identifies at least one position on the distal femur for facilitating completion of the surgical procedure to enhance at least one of range of motion, stability and patella tracking of the knee. Also, the adjustable femoral member can be configured to be movably couplable with at least one tibial member engaged with the proximal tibia to allow the knee to be moved through a range of motion without removing the femoral and tibial members. The stationary and adjustable femoral members can collectively comprise a femoral assembly which can be configured to be engaged with the tibial member described above or alternatively with another tibial member or prosthetic known in the art. In various embodiments, one or more of the at least one adjustable femoral member, the at least one stationary femoral member, and the at least one tibial member can comprise at least two members which can include lateral and medial members respectively.

Another embodiment provides a device for performing a minimally invasive surgical procedure on a knee comprising a femoral assembly engageable with a distal femur. The femoral assembly comprises a stationary femoral member removably attachable to the distal femur, an adjustable femoral member movably coupled with the stationary member to adjust tension in at least one ligament of or adjacent the knee and an adjustment mechanism coupled to the femoral assembly. The stationary member is engageable with a cut surface at the distal end of the distal femur and can have a cross sectional shape to correlate to a cross sectional shape of the cut surface.

The adjustable femoral member includes a medial portion and a lateral portion and at least one positioning feature that moves relative to the distal femur as the adjustable femoral member is adjusted and thus identifies at least one position on the distal femur for facilitating completion of the surgical procedure to enhance at least one of range of motion, stability or patella tracking of the knee. The adjustable femoral member is configured to be movably couplable with a tibial member engaged with a proximal tibia to allow the knee to be moved through a range of motion without removing the femoral and tibial members.

The adjustment mechanism can be coupled to the adjustable member and can include an actuator positioned proximate the medial or the lateral portion of the adjustable femoral member. In many embodiments the mechanism can be configured as an "opposing adjustment mechanism" in that the actuator is configured to adjust an opposite portion of the adjustable member to which the actuator is most closely positioned. In preferred embodiment the actuator is positioned on a medial side of the adjustable member to adjust a lateral portion of the member. The mechanism can adjust the adjustable femoral member relative to the stationary member and can do so throughout a range of motion of the knee without eversion or substantial displacement of the patella or other tendon. Movement of the adjustable member can be limited by means of a stop coupled to one of the adjustable member and/or the mechanism. The actuator can comprise an adjustment screw or nut and can also be configured to be actuated by an adjustment device such as a wrench or other hand held tool. Also the actuator and mechanism can be configured such that the surgeon can engage the actuator with the adjustment device to make adjustments to the adjustable member using a single hand, allowing the other hand free to manipulate the knee. This can be accomplished by configuring the actuator to be turned by torque from the unaided fingers or that from adjustment device. Further, the actuator and the adjustment device can be configured to allow the actuator to be actuated throughout a range of motion of the knee without physical or visual obstruction of the surgical field of the knee.

The stationary femoral member can include at least one access opening aligned with the at least one positioning feature of the adjustable member. The access opening can be configured to allow direct access to the femur through the positioning feature independent of a position of the adjustable femoral member relative to the stationary member. Also, the access opening can include a first opening aligned with a first positioning feature and a second opening aligned with a second positioning feature, wherein the openings provide access to the femur though both positioning features throughout a range of motion of the femoral assembly relative to stationary assembly.

In some embodiments, the stationary femoral member is engageable with a cut surface at the distal end of the distal femur. Similarly, in some embodiments the tibial member is engageable with a cut surface at the proximal end of the tibia.

Typically, the adjustable femoral member is adjustable from the medial side of the femoral member (e.g., by a medially positioned actuating device) to adjust tension in ligaments of the lateral side. However, the reverse configuration can be employed. Also, the adjustable member can be configured to adjust tension on the same side as the adjustable member. In some embodiments, for example those employing the opposing adjustment mechanism, the device can be configured such that adjustment on one side of the adjustable member causes the opposite side of the femoral member to rotate relative to the anterior and posterior aspects of the distal femur.

In various embodiments, the adjustable member can be adjusted via an adjustment member integral to adjustable member or a coupled actuator such as a side mounted actuator. In either approach, adjustment of the adjustable member may be accomplished using any suitable adjustment device or other adjustment means know in the art. In various embodiments, the adjustment means can include a hand held tool such as a wrench, a T-wrench, a torque wrench, a screw driver and the like. These devices can be configured to engage either adjustment member or the actuator disposed on the adjustable member or other portion of the femoral assembly. In one embodiment, the adjustment means can comprise a hand crank or similar device mechanically coupled to the adjustable member. In some embodiments the adjustable member can include at least one lateral adjustment member located and accessible from the medial side of the adjustable femoral member for adjusting a lateral portion of the adjustable member. The adjustment members can comprise screws, pins, levers, cams, spring-loaded members or any other suitable device(s) known in the art for conferring adjustability. In other embodiments, the adjustable femoral member may be partially or completely self-adjusting, for example via use of one or more spring-loaded or shape memory self-adjusting members or the like. In still other embodiments, the at least one adjustable femoral member comprises one or more pre-adjusted femoral members, each pre-adjusted femoral member conferring different amounts of ligament tensioning and balancing about the knee. A surgeon may choose any one of the pre-adjusted femoral members for balancing ligament tension, and may try more than one pre-adjusted member before deciding which to use. Thus, by the terms "adjustable," "adjustable femoral member," "adjustability" and the like it is meant that one or more members may be used to adjust ligament tension in the knee. In various embodiments, adjustability may be achieved via use of one or more adjustable members, self-adjusting members, interchangeable pre-adjusted members, combinations thereof or any other suitable devices.

In various embodiments, a device for performing and/or otherwise enhancing knee surgery may be used interchangeably for either a left knee or a right knee. In other words, some embodiments of a knee surgery device are not typically specific to either a left knee or a right knee, although such left-side-specific/right-side-specific devices are contemplated. Thus, because the typical knee balancing device of the present invention is used on either knee, the terms "medial" and "lateral" should not be interpreted as limiting a device to use for either a left knee or a right knee. For example, an adjustment member that is oriented laterally relative to a right knee will be oriented medially relative to a left knee.

In some embodiments, the at least one adjustable femoral member comprises at least one distal femoral portion for emulating the distal condylar surface of the femur and at least one posterior condylar portion to emulate posterior condylar surfaces of the femur. In some embodiments, the at least one posterior condylar portion comprises a fixed medial femoral posterior condylar portion acting as the fulcrum for the moveable lateral femoral posterior condylar portion. In some embodiments, the distal femoral portion, the medial femoral posterior condylar portion and the lateral femoral posterior condylar portion are all one piece comprising an integral structure which in an embodiment can be a single mold, casting or extrusion. In other embodiments, these portions may be multiple, coupled parts. The distal and posterior condylar portions allow the femoral member to movably engage with the tibial member to allow the knee to be moved through a range of motion while the device is engaged with the knee.

In some embodiments, the distal femoral portion and posterior condylar portions of the adjustable femoral member are movably couplable with one or more complementary depressions in the tibial member. For example, the posterior condylar members may comprise a medial femoral posterior condylar member slidably couplable with a medial depression of the tibial member and a lateral femoral posterior condylar member slidably couplable with a lateral depression of the tibial member.

In some embodiments, the at least one stationary femoral member comprises at least one distal femoral plate for coupling the distal femoral portion of the adjustable femoral member to the distal femur and at least one posterior condylar member wrapping around from the distal femoral portion to contact at least part of typically the lateral posterior femoral condyle and a lateral posterior femoral condyle of the distal femur. In such embodiments, the lateral femoral posterior condylar portion of the adjustable femoral member is separately adjustable relative to the lateral side of the stationary femoral member. In some embodiments, the distal femoral portion and posterior condylar members of the stationary femoral member may comprise one piece such as a single mold, extrusion or casting. In alternative embodiments, the stationary femoral member may comprise multiple coupled parts.

In various embodiments, the adjustable member may be adjustable in any number of ways (e.g., vertically, horizontally, pivotally etc.,) but in one embodiment it is configured to be adjustable relative to the stationary femoral member to separately adjust tension in the lateral collateral ligament of the knee, from an adjustment mechanism located on the medial side of the moveable femoral member. In making such adjustments via the opposing adjustment mechanism, the patella can remain in a non-everted position, such as is the case in minimally invasive TKA surgery, avoiding false influence on the ligaments otherwise caused by patella eversion.

When the adjustable femoral member is adjusted to adjust and balance ligament tension, the at least one positioning feature moves relative to the distal femur and the stationary member. The post-adjustment position of the positioning feature(s) provides positional information which may then be used for completing the TKA procedure. For example, such information may be used to position a cutting guide on the distal femur for making subsequent bone cuts, to make the bone cuts themselves, to apply the femoral prosthetic component to the distal femur, and/or the like. The positioning features themselves may comprise any of a number of different features, such as but not limited to one or more apertures, drill bit guides, surface markers, surface features, measurement devices, embedded markers, fiducials, transponders, transceivers and/or sensors.

In various embodiments two or more apertures can be used as the positioning features, with a specific embodiment of two apertures. In some embodiments, these apertures can be configured to rotate relative to the distal femur when the adjustable femoral member is adjusted. Additionally or alternatively, the apertures may move in an anterior and/or posterior direction relative to the distal femur. The apertures may provide information in a number of different ways. For example, they may act as drill bit guides to guide the drilling of holes into the distal femur for attachment of a cutting guide used to make one or more cuts in the distal femur and proximal tibia. Typically, such apertures extend through the adjustable member and through apertures in the stationary femoral member to the distal femur to allow for passage of the drill bit. Alternatively, fiducials, sensors, transmitters, markers or the like may be disposed in the apertures and may send or receive signals or act as markers for use by external devices. In one embodiment, for example, a robotic surgical system and/or a navigational system may use the position of such fiducials, sensors, markers or the like to help guide a surgical saw blade, bur or the like to shape the distal femur. Optionally, the apertures may be positioned slightly asymmetrically on the adjustable member to provide for a built-in desired flexibility in the ligaments, to achieve enhanced range of motion, stability, and patellar tracking of the prosthetic knee joint, when the surgical procedure is completed. In another embodiment, the at least one adjustable femoral member may be asymmetrically oriented relative to the stationary member to provide built-in desired flexibility in the ligaments, to achieve enhanced range of motion, stability, and patellar tracking of the prosthetic knee joint, when the surgical procedure is completed.

Any other suitable positioning feature or combination of features may be included in the adjustable femoral member, e.g. apertures, grooves, fiducials, markers etc. Furthermore, the positional information derived from such positioning features may be generated and used in any suitable fashion. For example, positional features may act as markers which may be queried by an external system, such as a navigational or robotic system. Positional information may then be generated and/or processed via a computer and data regarding post-adjustment positions, pressures, ligament tensions at various points in a range of motion may be provided to a user and/or to a robotic surgery device. Positional information may also be provided by mechanical means such as torque applied and adjusted to the adjustment mechanism of the adjustable member. Any suitable positioning feature may be used and any positional information, ligament tension information and/or the like may be generated by various embodiments of the invention.

Typically, the at least one tibial member is engageable with a cut surface of the proximal tibia. Examples of tibial members include without limitation shims, paddles, plates, bars, platforms and rods. In a preferred embodiment, a plurality of tibial shims are provided, having different thicknesses or heights, and any one of the plurality of shims may be selected for engaging with the cut surface of the proximal tibia to provide a desired amount of tension in the ligaments. Optionally, the at least one tibial member may further comprise a plate for removably attaching to the cut surface of the proximal tibia, wherein the plate is disposed between the cut surface and the same or another selected tibial shim.

In some embodiments, the femoral and tibial members are movably coupled via force provided by at least one ligament adjacent the knee. More specifically, in one embodiment the femoral and tibial members are coupled only via force provided by ligament force. This coupling of the femoral and tibial members by ligament force may be described as "dynamic" coupling. Such coupling helps allow ligament tension to be balanced with a device that resides primarily within the joint space and also allows for the natural movements, rotations and translations of the tibia and femur to take place as the knee is flexed through a range of motion, resulting in dynamic ligament tension balancing through a range of motion of the knee. Thus, in some embodiments the femoral and tibial members, when engaged with the distal femur and proximal tibia respectively, are disposed primarily within a joint space between the distal femur and the proximal tibia. In these and related embodiments, a patella of the knee may remain approximately in its anatomical position while the femoral and tibial members are engaged and the knee is moved through the range of motion during the TKA procedure. That is the patella need not be inverted. The movable coupling of the femoral and tibial members allows for flexion and extension of the knee through its range of motion. Moreover, these and related embodiments allow for one or more of the following acts to be done throughout the range of motion of the knee: i) observation of the space or gap between the femoral and tibial members; ii) adjustment of the adjustable member; iii) balancing of the ligament tension; and iv) dynamic balancing of the knee throughout the range of motion of the knee. By "range of motion," it is meant that the knee is moved from extension to flexion and/or from flexion to extension. In some embodiments, the range of motion comprises a range from approximately full extension of the knee to approximately full flexion of the knee. (in other embodiments the range of motion may be narrower).

Components of the femoral and tibial members may be manufactured from any materials or combinations of materials known in the art. In various embodiments, one or both of the stationary femoral member and the adjustable femoral member can comprise one or more of the following materials: plastics, thermoplastics, composites, carbon fiber composites, aluminum, stainless steel, metal composite, cobalt-chrome alloys, titanium, alloys thereof or other metals known in the biomaterial and implantable arts. In some embodiments, the femoral and/or tibial members may further include at least one grasping member for facilitating placement and/or removal.

In another aspect of the present invention, a system for enhancing a surgical procedure on a knee comprises at least one femoral member removably engageable with a distal femur and at least one tibial member removably engageable with a proximal tibia and movably couplable with the femoral member to allow the knee to be moved through a range of motion without removing the femoral and tibial members. The femoral member includes at least one stationary member for attaching to the distal femur and at least one adjustable femoral member movably coupled with the stationary member to adjust tension in at least one ligament of or adjacent the knee. The adjustable femoral member includes at least one positioning feature that moves relative to the distal femur as the adjustable femoral member is adjusted and thus identifies at least one position on the distal femur for facilitating completion of the surgical procedure to enhance at least one of range of motion, stability and patella tracking of the knee. Such a system may include any of the features described above.

As described above, adjustment of the at least one adjustable member may be accomplished by any suitable means. Thus, in various embodiments of the system the at least one adjustable femoral member may include one or more adjustable members, self-adjusting members, interchangeable pre-adjusted members, or any other suitable devices for conferring adjustability.

In still another aspect of the invention, an embodiment of a method for facilitating a surgical procedure on a knee involves: engaging at least one femoral member with a distal femur to movably couple with a tibial member engaged with a proximal tibia, the femoral member comprising at least one stationary member and at least one adjustable member; moving the knee; and adjusting the adjustable femoral member to apply tension to at least one of the ligaments of or adjacent the knee, thus moving at least one positioning feature of the adjustable femoral member relative to the distal femur to identify at least one position on the distal femur for facilitating completion of the surgical procedure.

Typically, though not necessarily, the tibial member is engaged with a cut surface of the proximal tibia, and the femoral member is engaged with a cut surface of the distal femur. As described above, in some embodiments the tibial and femoral members are engaged primarily within a joint space between the cut surfaces of the proximal tibia and the distal femur and are movably coupled via force provided by the at least one ligament adjacent the knee. This coupling of the femoral and tibial members by ligament force may be described as "dynamic" coupling. Such coupling helps allow ligament tension to be balanced with a device (e.g., a balancing and/or prosthetic device) that resides primarily within the joint space and also allows for the natural movements, rotations and translations of the tibia and femur to take place as the knee is flexed through a range of motion, resulting in dynamic ligament tension balancing through a range of motion of the knee.

In some embodiments, engaging the tibial member comprises includes the selection the tibial member from a plurality of tibial members with different dimensions, the selected tibial member having dimensions to apply a desired amount of tension to the at least one ligament. Engaging the femoral member, in some embodiments, involves attaching a stationary portion of the femoral member to the distal surface of the femur, with an adjustable portion of the femoral member being coupled with the stationary portion. In some embodiments, moving the knee comprises sliding at least one distal femoral condylar and posterior condylar member of the femoral member along at least one complementary depression in the tibial member. More generally, moving the knee may involve sliding the tibial member along the femoral member.

In some embodiments, moving the knee may involve moving from approximately full extension to approximately full flexion. Alternatively, moving the knee may involve moving from approximately full flexion to approximately full extension. In some embodiments, the knee may be moved between extension and flexion more than once, either before, after or during adjustment of the adjustable member of the femoral assembly. For example, in some embodiments the method may further involve moving the knee after the adjustment step and further adjusting the adjustable femoral member. Any combination of knee movements and adjustments is contemplated within the scope of the present invention. For example, a method may involve moving the knee through a range of motion to help determine the desired ligament tension balance in the knee during the range of motion. In some embodiments, at least the moving and adjusting steps are performed with the patella of the knee located approximately its anatomic position over the knee.

Adjusting the adjustable femoral member, in some embodiments, involves adjusting tension in at least one of a medial collateral ligament and a lateral collateral ligament. Sometimes adjusting the adjustable femoral member comprises enlarging a joint space between at least part of the distal femur and the proximal tibia to apply tension to at least one of the ligaments. In various embodiments, enlarging the joint space may involve enlarging the space primarily at a medial side of the knee or primarily at a lateral side of the knee. Typically, enlarging the space applies tension to the medial collateral ligament, the lateral collateral ligament or both. In some embodiments, adjusting the adjustable femoral member comprises moving an adjustable portion of the femoral member relative to a stationary portion of the femoral member. For example, adjusting the adjustable femoral member may involve adjusting at least one adjustment member or actuation device located on the medial side of the adjustable femoral member, designed to move the lateral side of the adjustable femoral member. In some embodiments, adjustment of the adjustable femoral member can be accomplished by turning of an adjustment screw or other actuating device coupled to an adjustment mechanism.

In some embodiments, adjusting the adjustable femoral member causes at least one positioning feature on the femoral member to be oriented to the distal end of the femur, the positioning feature(s) helping determine a position for applying a cutting guide to the distal femur, for orienting a surgical navigation system sensor, for locating and or making subsequent bone cuts, or the like. In some embodiments, for example, the at least one positioning feature comprises one or more apertures for guiding a drill bit for forming one or more drill holes used to attach a cutting guide, for dynamically orienting a bone cutting device, for dynamic placement of fiducials or markers to orient a surgical navigation system sensor to the distal end of the femur, or the like. In some embodiments, the least one aperture comprises at least two apertures, and adjusting the adjustable femoral member causes the at least two apertures to rotate relative to one another over the distal end of the femur. For example, the apertures may rotate about an axis approximately corresponding to a long axis of the distal femur. Alternatively or additionally, adjusting the adjustable femoral member may cause the at least one aperture to move in an anterior or posterior direction relative to the distal femur. Of course, as described above, any suitable positioning features may be included on the adjustable member, and any methods for acquiring or using positional information may be employed in various embodiments.

In some embodiments, the method may further comprise placing at least one hole or slot in the distal end of the femur, using the at least one aperture to guide a tool bit; removing the adjustable femoral member from the distal femur; using the at least one hole for attaching a cutting guide to the distal end of the femur; and making at least one cut on the distal end of the femur. Optionally, such a method may further include attaching a femoral prosthesis component to the cut distal end of the femur and attaching a tibial prosthesis component to a cut surface of the proximal tibia. In alternative embodiments, the method may further include sending one or more signals from the at least one positioning device to a distal femur cutting device and cutting the distal femur with the cutting device, based on or otherwise responsive to the signal(s). Such signals, for example, may be used as part of a navigational system and/or robotic surgical system.

Further details of these and other embodiments are described more fully below, with reference to the attached drawing figures.

BRIEF DESCRIPTION OF THE DRAWINGS

FIGS. 15A-15J are frontal perspective views schematically illustrating the method flow charted in FIG. 14. FIG. 15J also illustrates the reduction in incision size achievable using embodiments of the minimally invasive TKA surgical methods provided by the invention.

DETAILED DESCRIPTION OF THE INVENTION

Embodiments of the present invention provide devices, systems and methods for use in total knee arthroplasty (TKA) surgical procedures. However, various embodiments of the invention may be adapted for use with other knee surgery procedures or orthopedic surgical procedures on other joints, such as an elbow joint, shoulder joint or hip replacement. Additionally many embodiments are applicable to various minimally invasive orthopedic surgical procedures known in the art.

Various embodiments of the invention provide devices, systems and methods that can be employed to assist a surgeon in balancing ligament tension in a knee during a TKA procedure and thereby help the surgeon perform the TKA so as to achieve a desired ligament balance upon completion of the surgery. In particular various embodiments of the invention facilitate dynamic balancing of ligaments of the knee, such that these ligaments remain balanced through a range of motion about the knee. Such dynamic balancing in turn facilitates a surgical outcome in which the prosthetic knee has a desirable level of stability, patellar tracking and range of motion. These performance characteristics result in a more beneficial clinical outcome for the patient in terms of improved gait and mobility including the ability to negotiate uneven surfaces such as stairs. Additionally, the long term biocompatibility of the prosthetic knee is improved (e.g. reduced swelling, inflammatory response/tissue and pain) as a result of the improved fit of the balanced prosthetic knee.

Figure 1A:
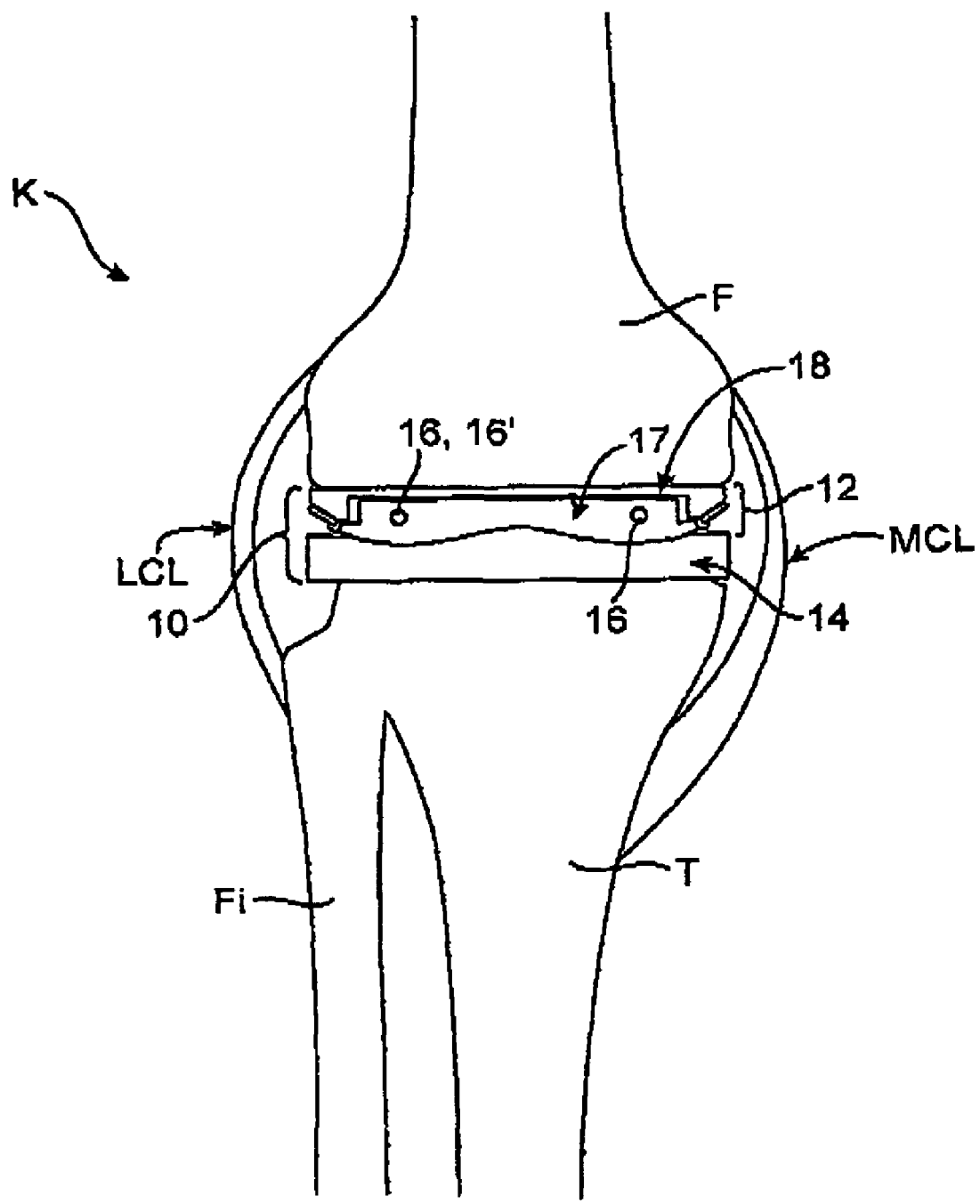
FIG. 1A is a frontal view of a knee in extension, with a knee balancing device according to one embodiment of the invention in place within the knee joint.

With reference now to FIG. 1A, a frontal view of a right knee K is shown in extension, with a knee balancing system 10 in place within the knee joint space. The anatomical components of the knee K that are pertinent to this description include a distal femur F, a proximal tibia T, a medial collateral ligament MCL, and a lateral collateral ligament LCL. (Also labeled is the proximal fibula Fi, to which the LCL attaches.) The knee K is shown without a patella, medial collateral ligament or lateral collateral ligament, for clarity, but many embodiments may be used while the patella is in its anatomical position on the anterior aspect of the knee K. In FIG. 1A, a portion of the distal end of the distal femur F and a portion of the proximal end of the proximal tibia T have been cut or shaved off, to create level surfaces on which to place a femoral member 12 and a tibial member 14, respectively, of dynamic knee balancing system 10. Femoral member 12, also described as femoral assembly 12, can comprise adjustable femoral member 17, an adjustment member 16 and a stationary femoral member 18. As described herein adjustment member 16 allows adjustment of adjustable member 17 relative stationary member to 18 so as to balance knee K through its range of motion. In various embodiments, a knee balancing device may be provided as only a femoral member, for example to be used with off-the-shelf tibial trial inserts. In other embodiments, a knee balancing system 10 may provided which comprise a femoral member 12 and tibial member 14.

In the embodiment shown, femoral member 12 is adjustable to adjust tension in the MCL, the LCL, or both. Adjustability may be achieved by any suitable means, some of which are described in more detail above and below. In one embodiment, for example, one or more adjustment members 16, which may comprise screws, pins, levers, spring-loaded mechanisms, shape memory materials or the like, that are coupled with femoral member 12 to provide adjustability. Suitable springs for the spring loaded mechanisms can include one or more of coil spring, leaf springs, flat springs, clock springs or other spring known in the art. Suitable shape memory materials can include NITINOL and other nickel titanium alloys known in the art. In some embodiments, adjustment members 16 may be used for separately adjusting femoral member 12 on either side to separately adjust tension in the MCL or the LCL.

In some embodiments, adjustment member 16 can comprise a self adjustment member 16'. Self-adjustment member 16' can employ the use of one or more springs or spring loaded mechanisms. Suitable springs for self-adjustment mechanism 16' can include one or more of coil springs, leaf springs, flat springs, clock springs or other spring known in the art. In a preferred embodiment, self-adjustment mechanism 16' uses a clock spring. Self-adjustment mechanism 16 desirably exerts sufficient spring or other force on the tendons adjacent the knee to put the tendons in tension. The spring force of mechanism 16' can be selected to put the tendons of the knee in sufficient tension so as to balance the knee of the individual patient through the range of motion of the knee. Such balancing allows enhancement of one or more of the range of motion, stability or patella tracking of the knee Selection of the appropriate spring force can be achieved by measurement of the tension of the tendon using force or strain gauges or sensors described herein or known in the art combined with visual observation or measurements of the fit between the adjustable member 17 and tibial members 14 through the range of motion of the knee.

Femoral member 12, tibial member 14 and any of their component parts may be manufactured from a variety of suitable materials. In various embodiments, femoral member 12 and/or tibial member 14 may be manufactured from one or more plastics, composites and/or metals, such as aluminum, stainless steel, composite, cobalt-chrome, titanium, or the like. These or any other suitable material(s) and combinations of materials may be used in various embodiments.

As shown in FIG. 1A and subsequent figures, knee balancing system 10 is typically disposed primarily within the joint space of knee K during a TKA surgery, thus providing for more convenient manipulation of the knee, anatomical positioning of the patella during surgery and the like. In alternative embodiments, however, a knee balancing device or system could be engaged with the knee at a location external to the knee joint. For example, in one embodiment, the device may comprise an externally applied frame that performs the same functions as the devices described herein. In such embodiments, some or all of the knee balancing device may be located external to the knee joint, thus not fitting within the knee joint space during the surgical procedure.

Figure 1B:
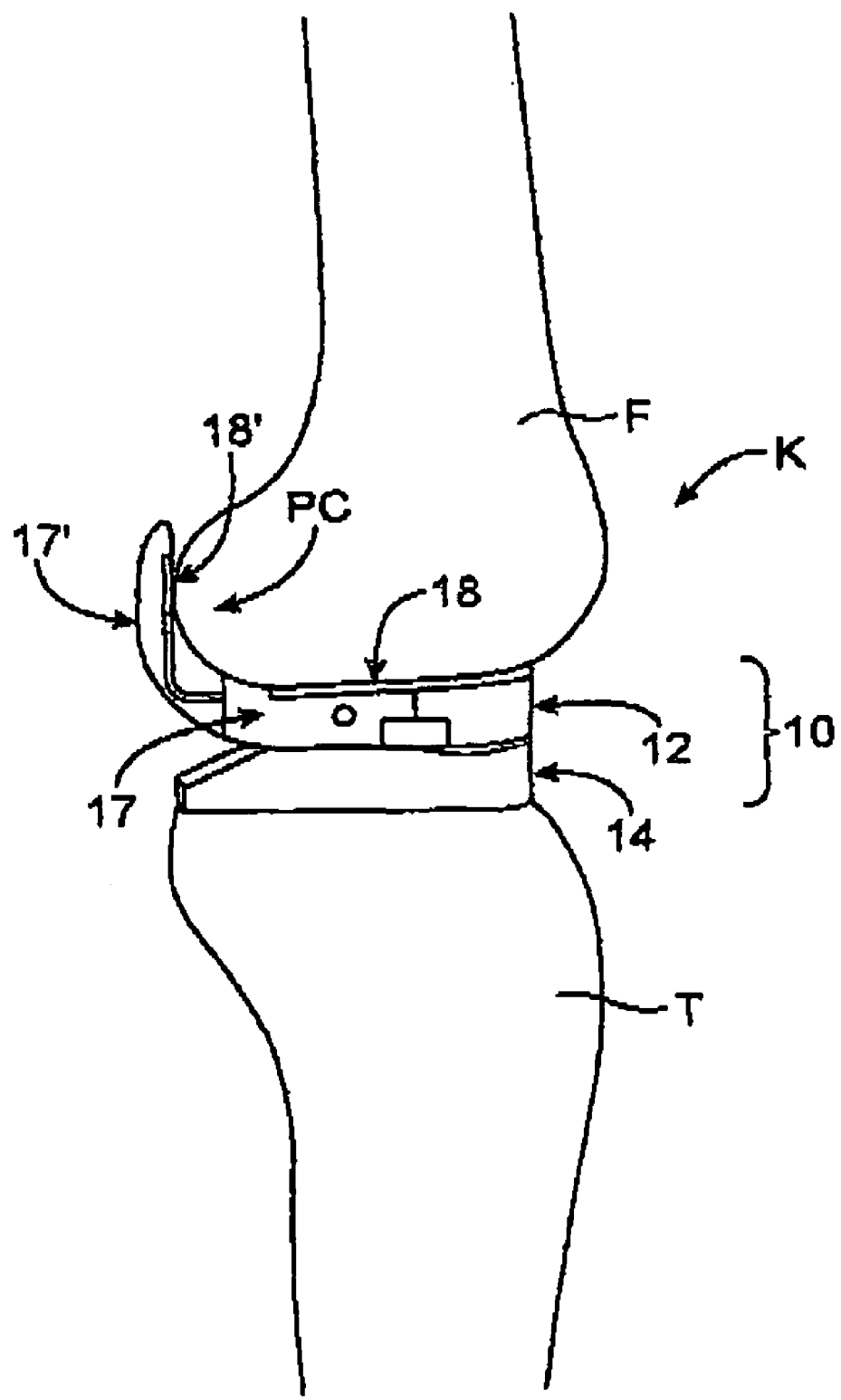
FIG. 1B is a side view of the knee in extension and knee balancing device shown in FIG. 1A.

Referring now to FIG. 1B, the knee K is shown from a side view. In this and subsequent figures, the collateral ligaments MCL and LCL, other ligaments such as the posterior cruciate ligament PCL, and the fibula Fi are removed for clarity. As is visible in this view, femoral member 12 suitably comprises a stationary femoral member 18 and an adjustable femoral member 17. Stationary femoral member 18 is typically removably attached to a surface of the distal femur F, often a cut surface at the distal end of the distal femur F, and adjustable femoral member 17 is coupled with stationary femoral member 18. Stationary femoral member 16 includes at least one stationary posterior condylar member 18' extending posteriorly to contact at least one of the medial and lateral posterior condyles PC of the distal femur F. Typically, stationary femoral member 18 includes two stationary posterior condylar members 18', one for each posterior condyle PC. Similarly, adjustable femoral member 17 suitably includes one or more (preferably two) adjustable posterior condylar members 17' extending posteriorly to emulate the two posterior condyles PC. As is described more fully below, posterior condylar members 17', 18' allow femoral member 12 to be adjusted to balance ligament tension in the knee K and also allow knee balancing system 10 to remain in place within the joint space while the knee K is moved through a range of motion. In various embodiments, stationary femoral member 18 and stationary posterior condylar members 18' may be either multiple, couple parts or may be one piece or extrusion. Similarly, adjustable femoral member 17 and adjustable posterior condylar members 17' are all one piece or extrusion in some embodiments, but may alternative comprise multiple coupled parts.

Typically, adjustable femoral member 17 is movably engageable with tibial member 14 to allow knee balancing system 10 to remain in place within the knee joint space while the knee K is moved through a range of motion. In some embodiments, such as the one shown in FIG. 1A and subsequent figures, adjustable femoral member 17 and tibial member 14 are movably engaged with one another via force applied by the ligaments of the knee K, especially the MCL and LCL. In other words, femoral member 12 and tibial member 14 are two separate components which are brought together into a movable/slidable coupling by the application of ligament force. Such coupling of adjustable femoral member 17 and tibial member 14 via ligament force provides for dynamic balancing of the knee through a full range of motion of the knee. In various alternative embodiments femoral member 12 and tibial member 14 can be coupled solely via a passive mechanical coupling or a combination of mechanical and ligament force coupling.

Figure 1C:
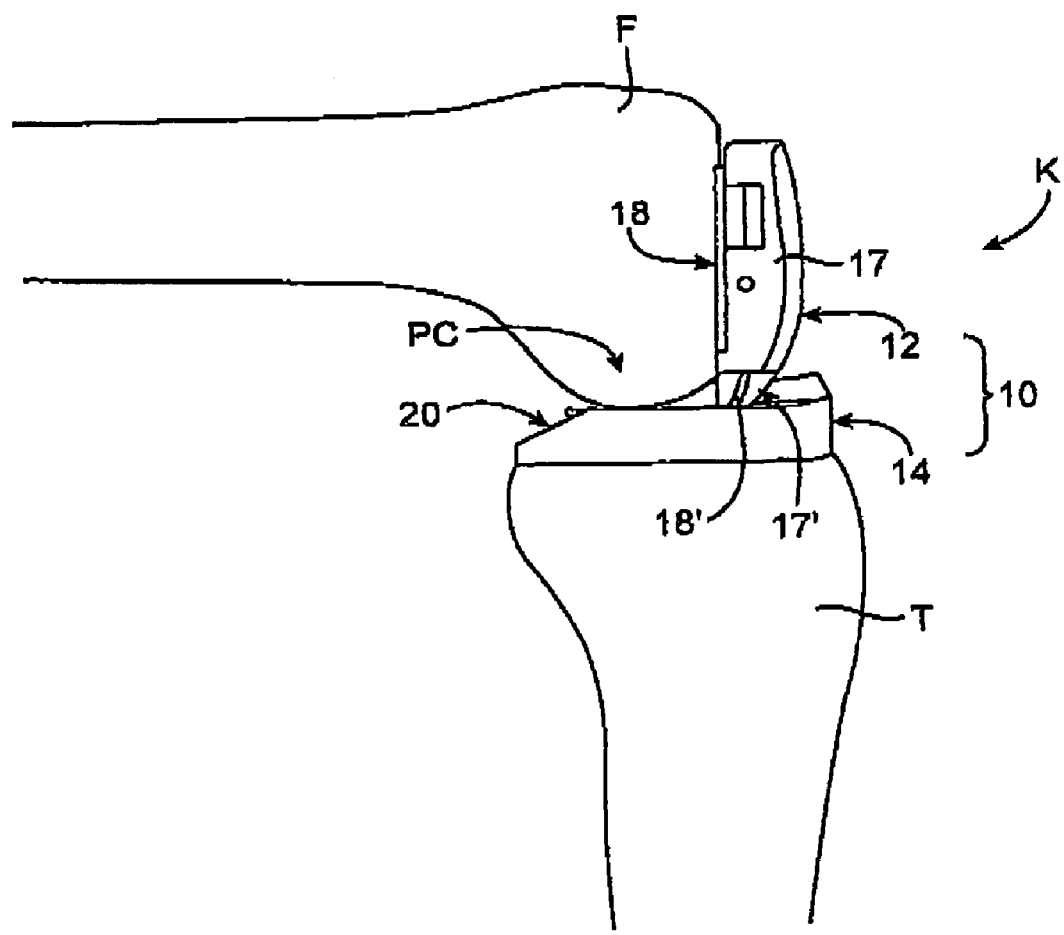
FIG. 1C is a side view of the knee and knee balancing device shown in FIGS. 1A and 1B, with the knee in a position of flexion.

With reference now to FIG. 1C, knee balancing system 10 is shown with the knee K in flexion. It can be seen here that stationary posterior condylar member 18' and adjustable posterior condylar member 17' are slidably engageable with complementary one or more grooves 20 on tibial member 14. Thus, knee balancing system 10 is movable/slidable through approximately a full range of motion of the knee K, from full extension to full flexion and vice versa. In use, these and related embodiments allow knee K to be movable through the full range of motion of the knee.

Figure 1D:
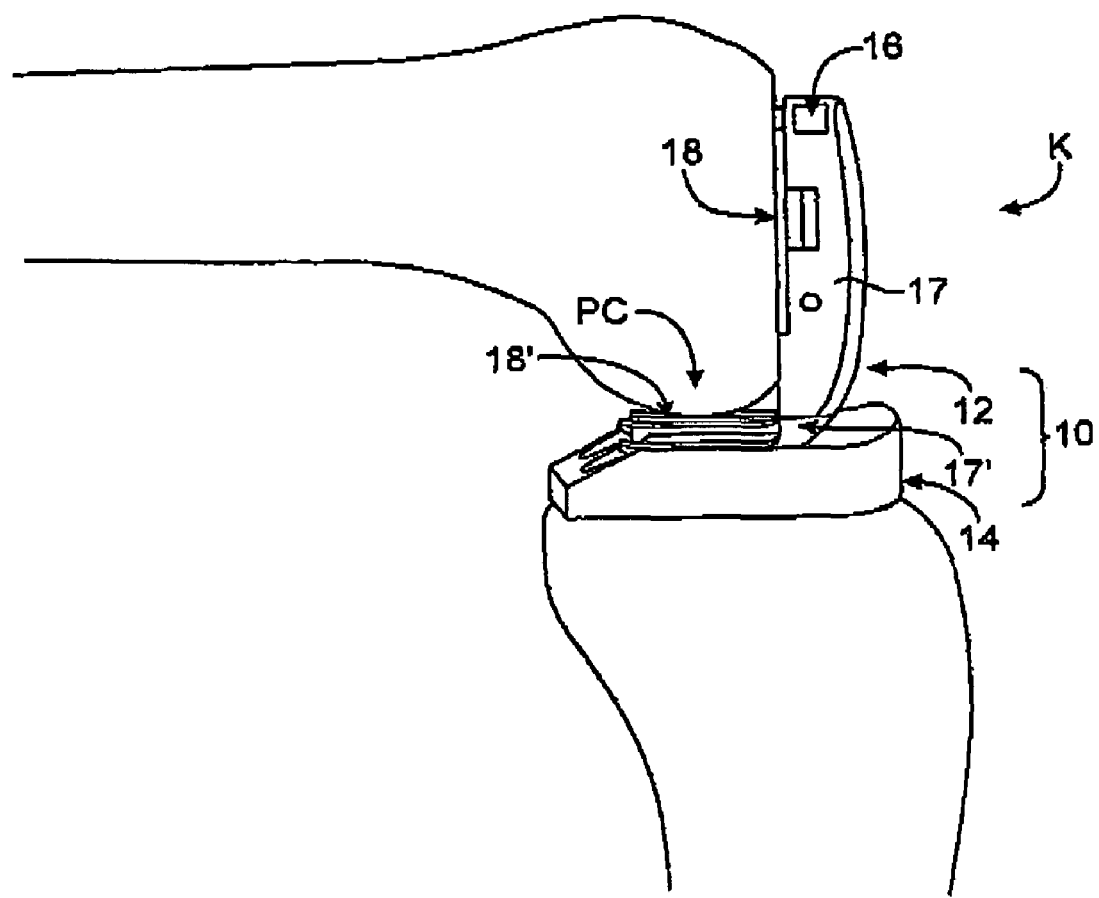
FIG. 1D is a side view of the knee and knee balancing device shown in FIGS. 1A-1C, with the knee balancing device adjusted to achieve a desired ligament tension balance according to one embodiment of the invention.

Referring to FIG. 1D, knee balancing system 10 is shown after an adjustment has been made to adjustable femoral member 17. In one embodiment, adjustable femoral member 17 is separately adjustable on either side to separately adjust tension in the MCL and/or the LCL. Such adjustment(s) may be achieved by any suitable means, such as manual adjustment via a screw or other adjustment member, self-adjustment via a spring-loaded mechanism, or the like. In the embodiment shown, adjustment member 16 is adjusted to move adjustable femoral member 17 relative to stationary femoral member 18. As adjustment member 16 is adjusted, adjustable femoral member 17 rotates relative to stationary femoral member 18, thus causing adjustable posterior condylar member 17' to move away from stationary posterior condylar member 18'. This movement creates a larger joint space on the side of adjustment, thus tightening the collateral ligament on that side. Meanwhile, the distal femoral portion of adjustable femoral member 17 has rotated relative to the distal femoral portion of stationary femoral member 18, approximately about the long axis of the femur F. If adjustment members 16 on both sides of adjustable femoral member 17 are adjusted in the same direction, adjustable femoral member 17 may be caused to move anteriorly or posteriorly relative to stationary femoral member 18. Thus, adjustable femoral member 17 may be adjusted rotationally as well as in an anterior/posterior orientation.

Figure 1E:
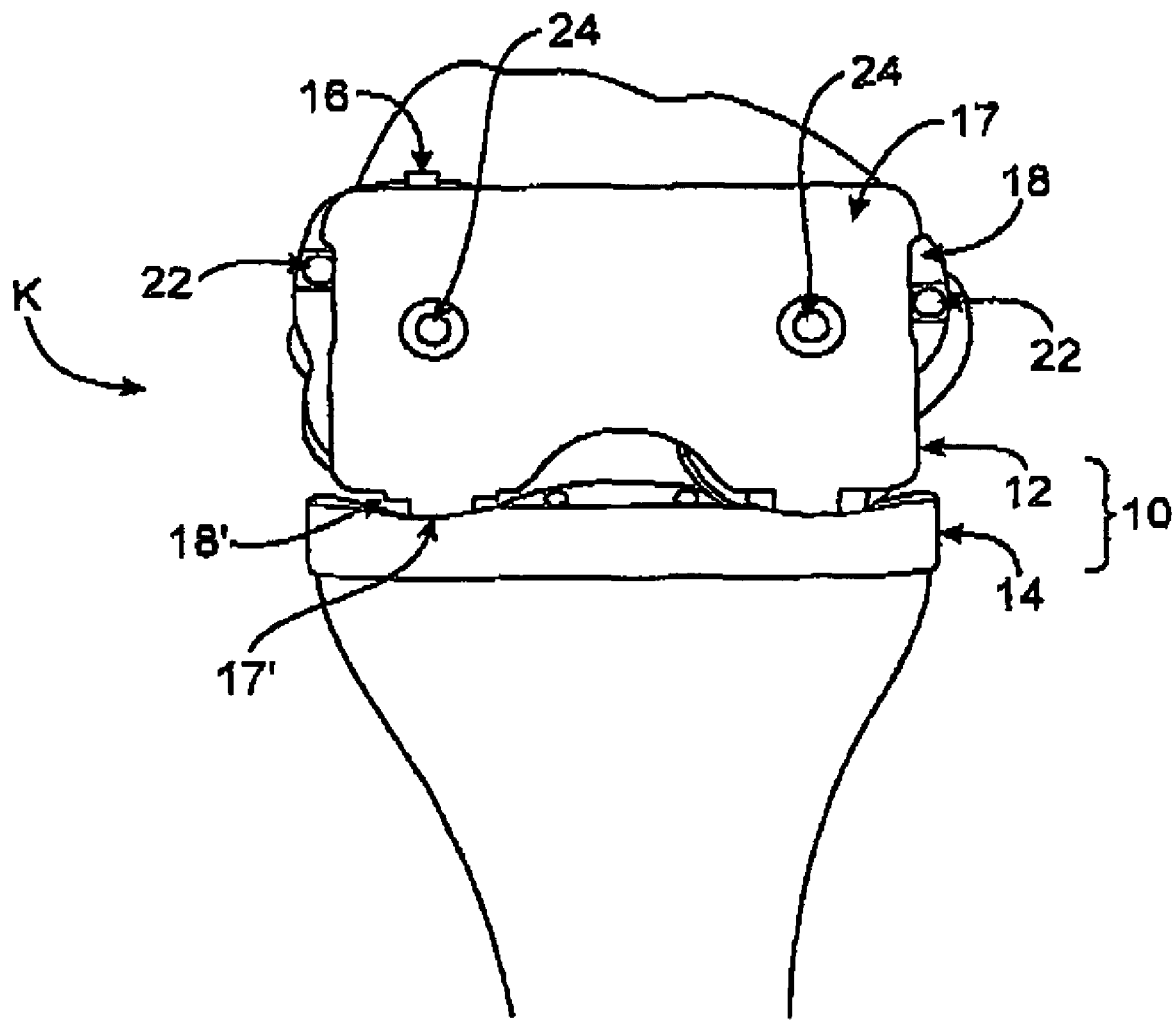
FIG. 1E is a frontal view of the knee and knee balancing device shown in FIGS. 1A-1D, with the knee balancing device adjusted to achieve a desired ligament tension balance according to one embodiment of the invention.

With reference now to FIG. 1E, the knee K and knee balancing system 10 of FIG. 1D is shown in frontal view. Here it can be seen that adjustment of adjustment member 16, on the lateral side of the distal femur F, has caused adjustable posterior condylar member 17' on the lateral side to move away from stationary posterior condylar member 18' on the lateral side, thus increasing the height of the joint space on the lateral side and rotating adjustable femoral member 17 slightly, relative to the distal femur. Adjustable femoral member 17 includes at least one positioning feature for providing positional information for facilitation the TKA procedure. As described above, the positioning feature(s) may include any of a number of different features, such as apertures, surface markers, embedded markers, fiducials, transmitters, transponders, transceivers, sensors and/or the like. These positioning features provide positional information that can then be used to facilitate the TKA procedure. For example, apertures may act as drill bit guides for drilling holes to apply a cutting guide to the femur F to make subsequent bone cuts. In another embodiment, apertures may contain fiducials or markers to provide information to a navigational system and/or robotic surgical system for positioning subsequent bone cuts or otherwise shaping the distal femur F via milling, burring or the like. Various embodiments have been fully described above, and any suitable positioning features and positional information may be used in various embodiments.

In the embodiment shown, adjustable femoral member 17 includes two apertures 24 as positioning features. Apertures 24 extend through adjustable femoral member 17 and also through stationary femoral member 18 such that apertures 24 may be used to guide a drill bit to form holes in the distal femur F. Of course, as just discussed, apertures 24 can serve any of a number of other functions, such as carrying fiducials, sensors, markers or the like. In some embodiments, corresponding apertures in stationary femoral member 18 are large enough to allow for movement of apertures 24 on adjustable femoral member 17 such that apertures 24 extend all the way to the cut surface of the distal femur F. When apertures 24 are used to drill holes for a cutting guide, the balancing system 10 is removed, holes are used to attach a cutting guide to the distal femur F, and the cutting guide used to make subsequent bone cuts on the femur F. Once these bone cuts are made, a femoral prosthetic component is typically placed on the cut distal end of the femur. These final bone cuts thus determine the position and orientation of the femoral prosthetic component. Alternatively, positioning information may be used to orient/position bone cuts by some other means (not using a cutting guide), such by guiding a saw blade, rotary cutter, bur or the like to make the actual bone cuts. In some embodiments, position information may be used to guide a robotic surgical system, to enhance the procedure via a navigational system, or the like.

Also shown in FIG. 1E are two stationary femoral member attachment screws 22. These screws are used to removably attach stationary femoral member 18 to the distal femur F. Any other suitable attachment device(s) may be used instead of or in addition to attachment screws 22 to attach stationary femoral member 18 to the distal femur F For example, adhesives, pins and/or the like may be used in some embodiments.

Figure 2B:
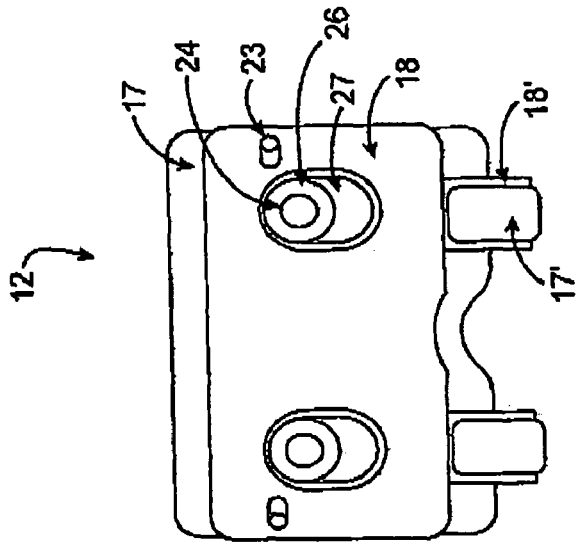
FIG. 2B is a rear view of the knee balancing device shown in FIG. 2A.
Figure 2C:
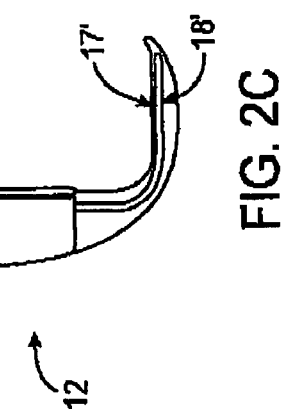
FIG. 2C is a side view of the knee balancing device shown in FIGS. 2A and 2B.
Figure 2A:
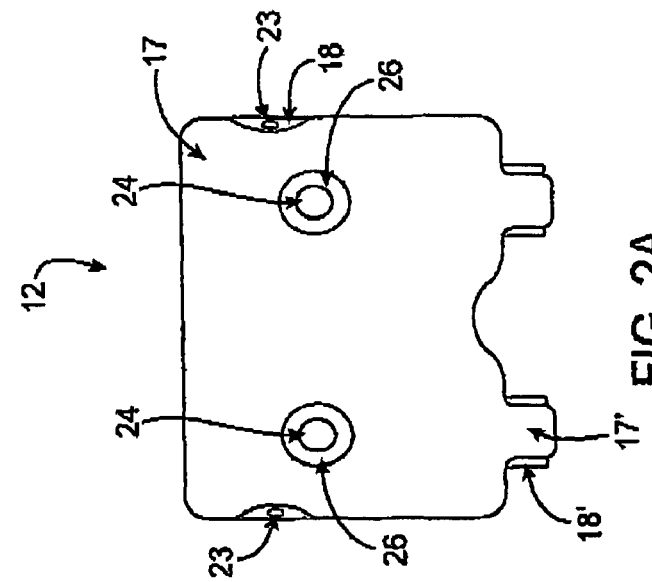
FIG. 2A is a frontal view of a knee balancing device according to one embodiment of the present invention.

FIGS. 2A-2C are anterior, posterior and side views, respectively, of an embodiment of femoral member 12. These figures show two screw holes 23 used for attaching stationary femoral member 18 to a distal femur. They also show drill guide apertures 24 which are formed by bushings 26 coupled with adjustable femoral member 17 and stationary femoral member 18. Bushings 26 move along slots 27 in stationary femoral member 17 as femoral member 12 is adjusted.

Figure 3A:
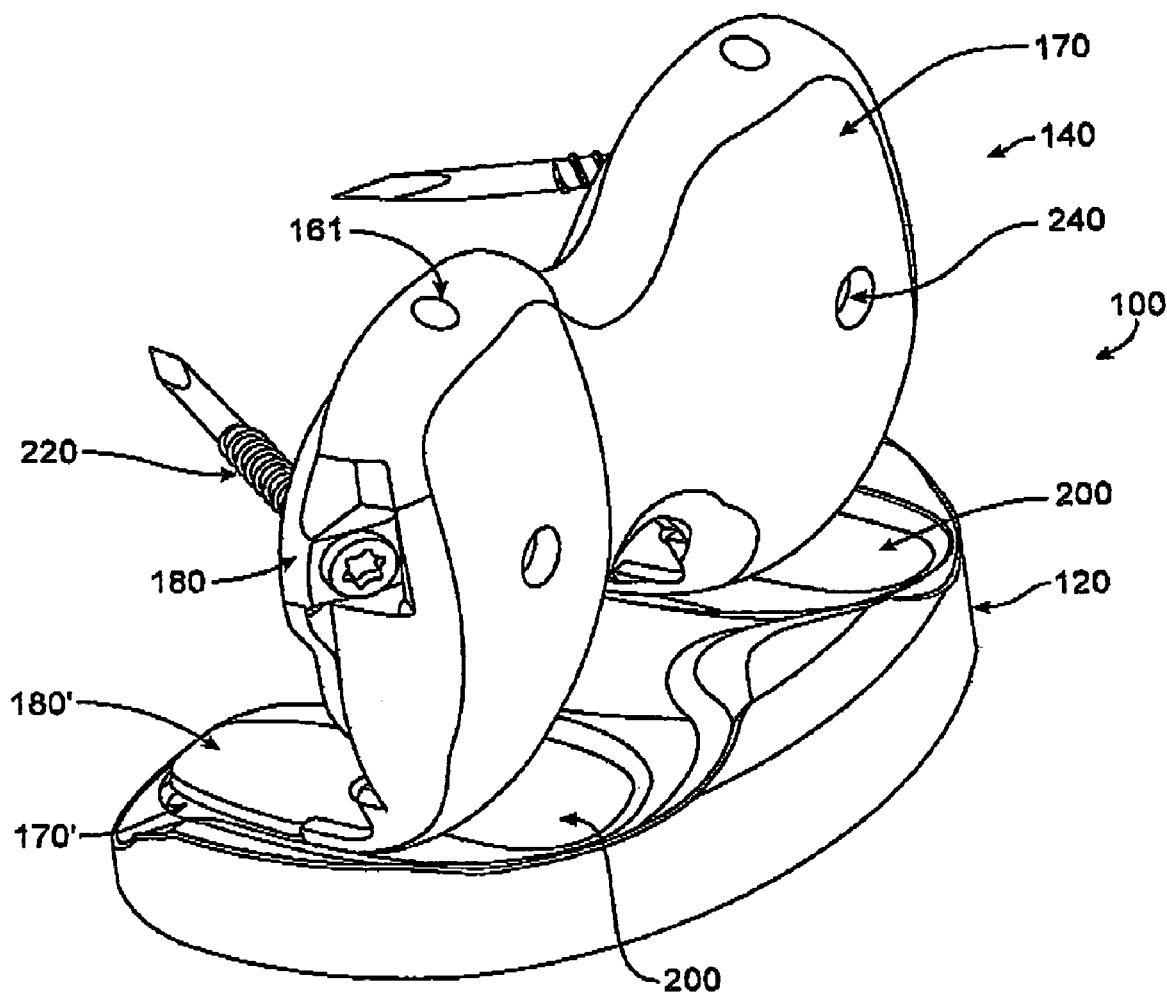
FIG. 3A is a front-perspective view of a knee balancing device according to one embodiment of the present invention.
Figure 3B:
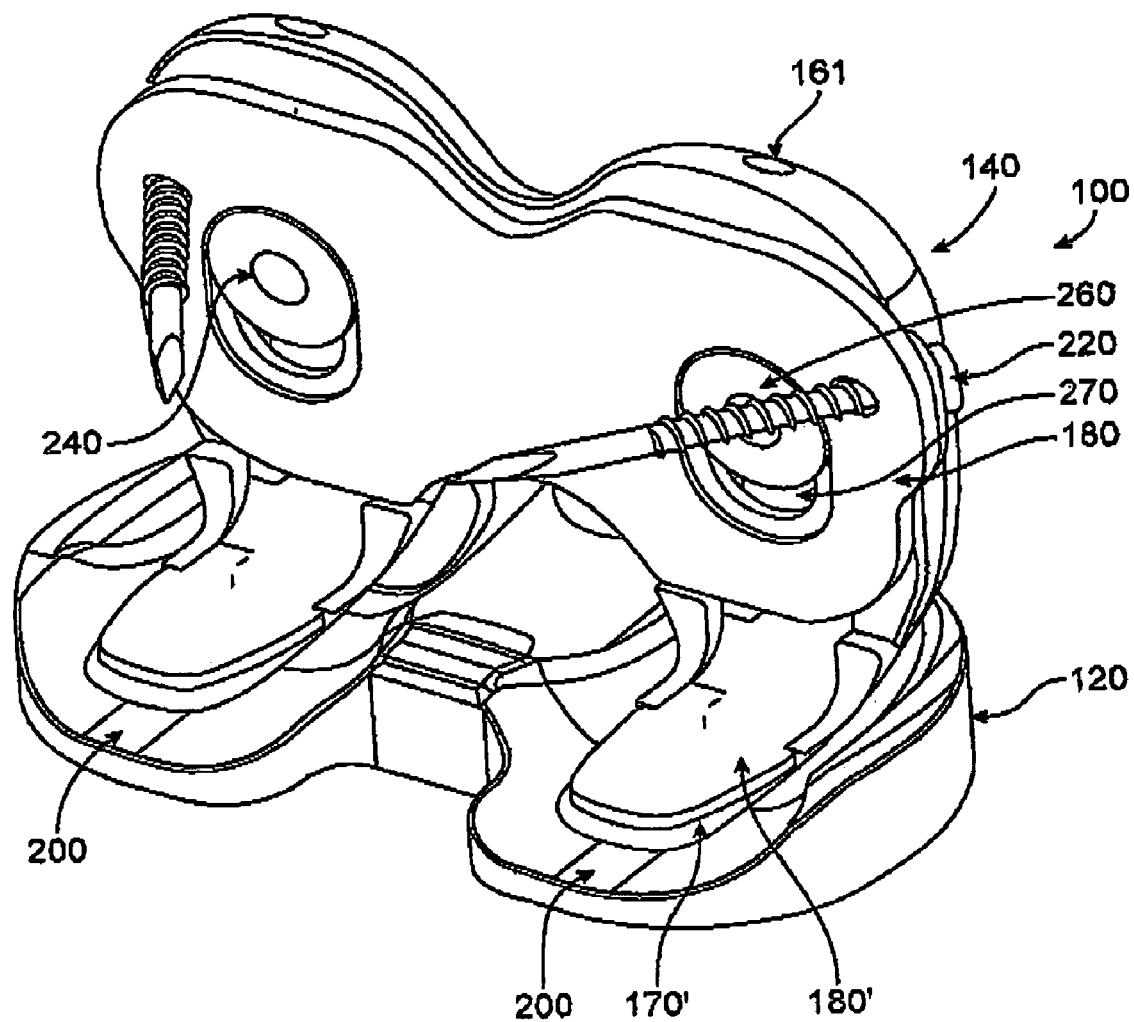
FIG. 3B is a rear-perspective view of the knee balancing device shown in FIG. 2A.

With reference now to FIGS. 3A and 3B, anterior and posterior perspective views, respectively, of an embodiment of a knee balancing system 100 are shown. Knee balancing system 100 suitably includes a femoral member 140 and a tibial member 120. Femoral member 140 may further include an adjustable femoral member 170 having adjustable posterior condylar members 170' and a stationary femoral member 180 having stationary posterior condylar members 180'. In some embodiments, adjustable femoral member 170 and adjustable posterior condylar member 170' will be one unitary piece or extrusion, while in other embodiments they may be two or more coupled pieces. Similarly, stationary femoral member 180 and stationary posterior condylar member 180' may comprise a one-piece construction or multiple pieces coupled together. In the embodiment shown, stationary femoral member 180 comprises a distal femoral plate coupled with two stationary posterior condylar members 180'. Any suitable configuration, combination or manufacturing process may be used in various embodiments.

Femoral member 140 may further include adjustment screw holes 161 for ingress/egress of adjustment screws (not shown), attachment screws 220, drill guide apertures 240, bushings 260, slots 270 and/or any other features described previously above. Tibial member 120 may suitably include two grooves 200 or depressions to provide for slidable coupling with femoral member 140. Generally, any of the features described above may be applied to knee balancing system 100.

Figure 3C:
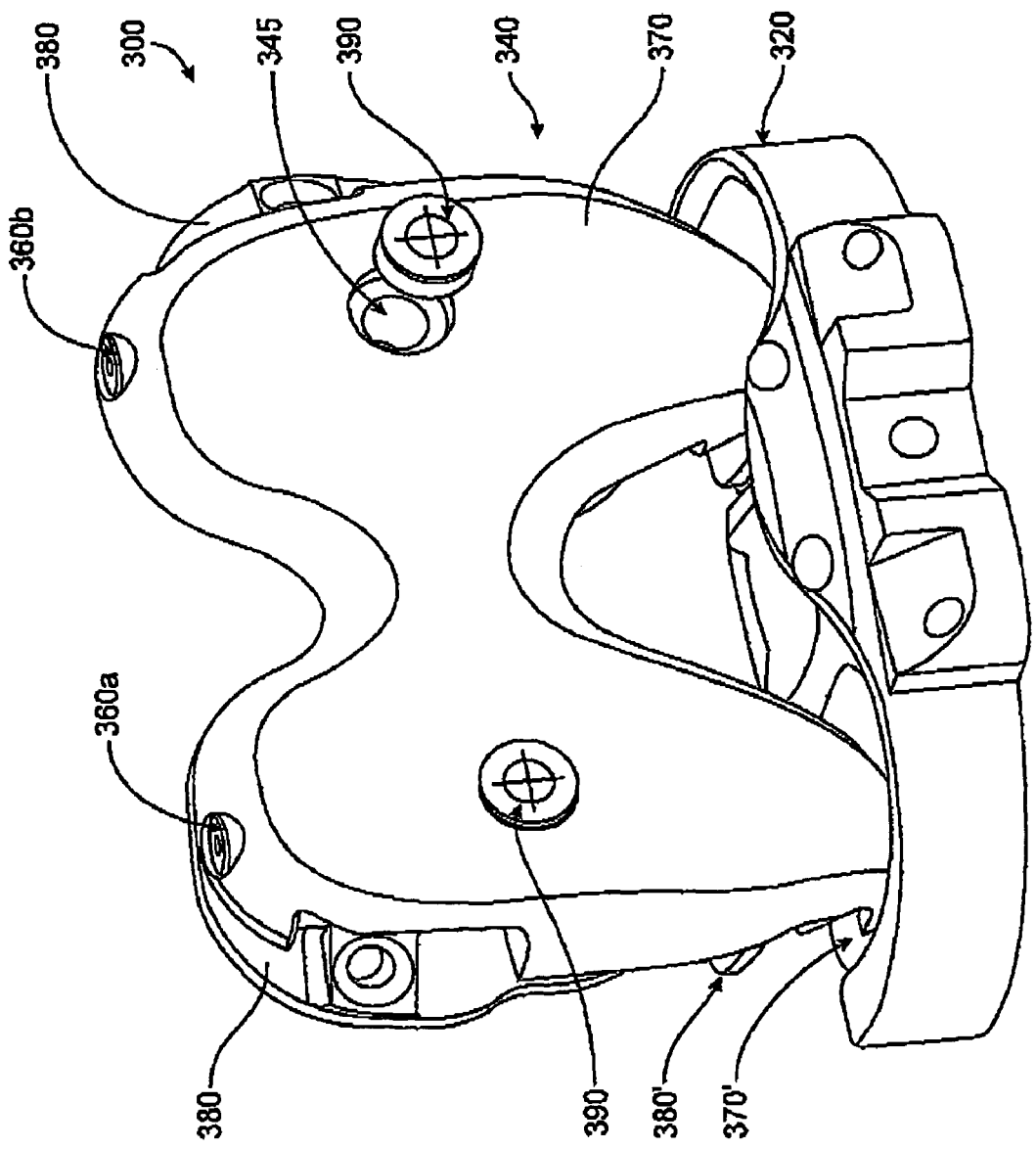
FIG. 3C is a front-perspective view a knee balancing device according to another embodiment of the present invention

Referring now to FIG. 3C, a knee balancing system 300 similar to that described above is shown in frontal-perspective view. System 300 includes a tibial member 320 and a femoral member 340, the femoral member 340 including an adjustable member 370 coupled with a stationary member 380. Adjustable member 370 includes two adjustable posterior condylar members 370', and stationary member 380 includes two stationary posterior condylar members 380'. In FIG. 3C, one adjustment member 360*a* has been adjusted to move adjustable posterior condylar portion 370' away from stationary posterior condylar member 380' on that side, which would increase the height of the joint space on that side if the device were in a knee joint, and would also rotate adjustable femoral member 370 slightly relative to the distal femur. The pictured embodiment includes two apertures 345 as positioning features, and disposed within apertures 345 are two fiducials 390 (or markers, sensors or the like) for providing positional information to a computer navigation system or robotic surgery system. Such positional information, for example, may include a dynamically balanced orientation of the knee to make subsequent bone cuts on the femur F.

Figure 4A:
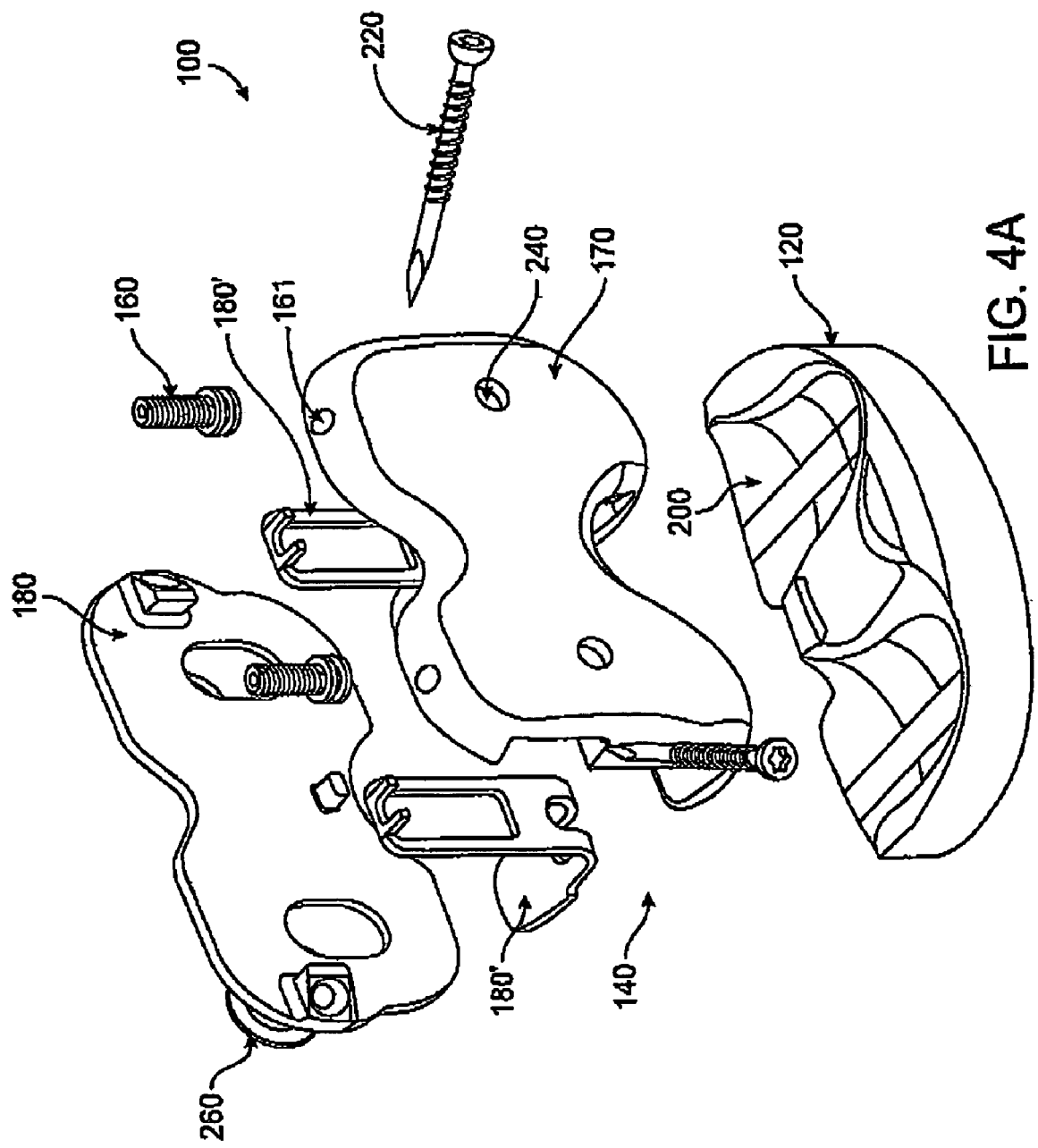
FIG. 4A is a front-perspective, exploded view of a knee balancing device according to one embodiment of the present invention.
Figure 4B:
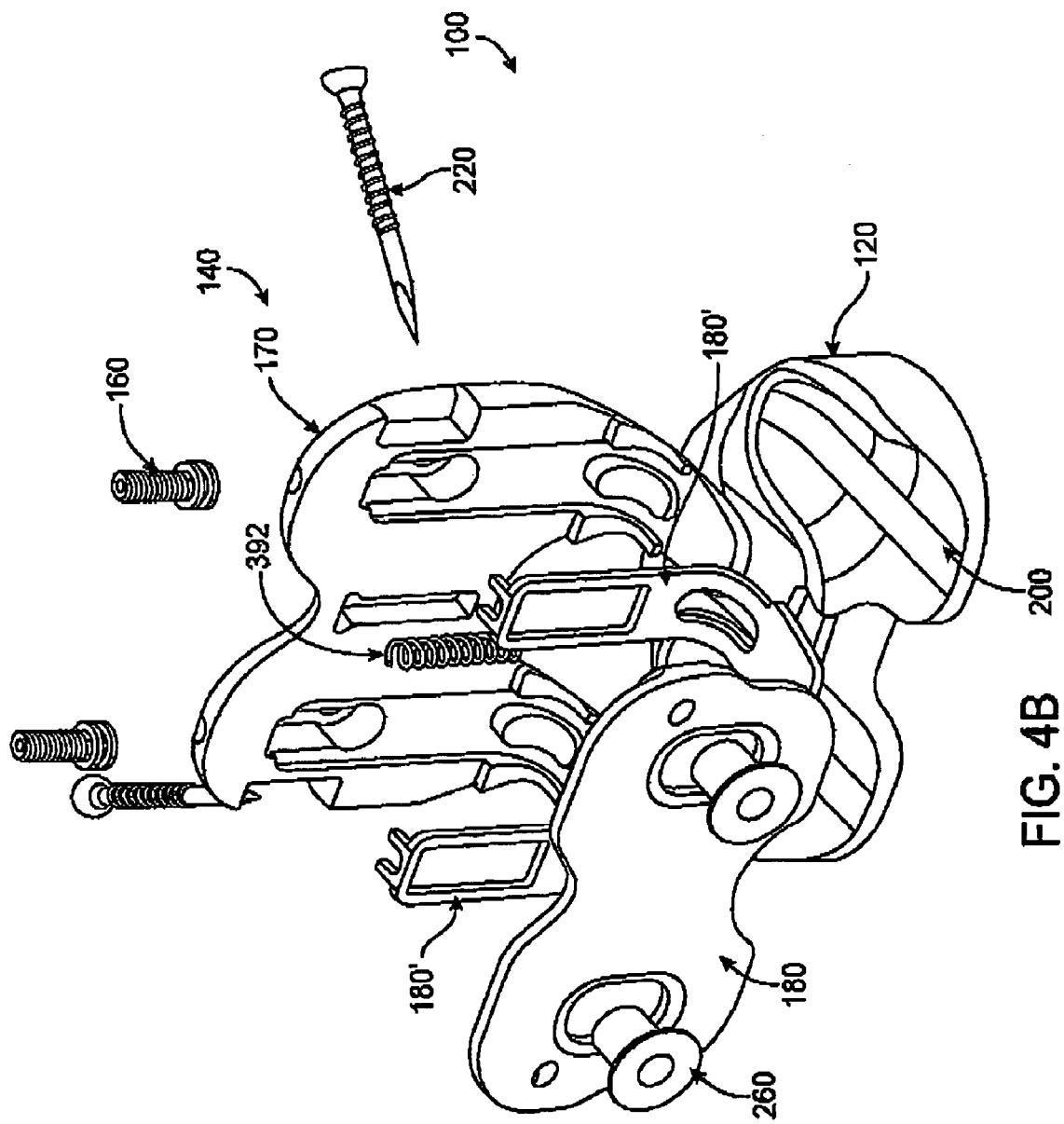
FIG. 4B is a rear-perspective, exploded view of the knee balancing device shown in FIG. 4A.

With reference now to FIGS. 4A and 4B, the embodiment of knee balancing system 100 from FIGS. 3A and 3B is shown in exploded view to more clearly show its component parts. In this embodiment, the component parts of knee balancing system 100 are the same as those shown and described above in reference to FIGS. 3A and 3B. It can be seen in FIGS. 4A and 4B that stationary femoral member 180 may comprise three coupled parts—a stationary femoral member distal plate 180 and two stationary posterior condylar members 180'. Such parts may be coupled by any suitable means, such as pressure fitting, sandwiching condylar members 180' between plate 180 and adjustable femoral member 170, screws, adhesives, and/or the like. Alternatively, stationary femoral member 180 may comprise one unitary piece or extrusion.

An additional part shown in FIG. 4B is a bias spring 392. Bias spring 392 may be incorporated into femoral member 140 to allow for rotation of adjustable femoral member 170 relative to stationary femoral member 180. Alternative embodiments of knee balancing system 100 may include any other suitable mechanism for allowing such rotation, anterior-posterior adjustment, and/or any other suitable adjustment(s).

In an exemplary method for enhancing a TKA procedure, a femoral member is typically removably engaged with a distal femur of a knee. Usually, the distal femur will have been cut to form a surface for engaging the femoral member, but this is not required in all embodiments. A tibial member is also engaged with a proximal tibia of the knee, usually a cut horizontal surface of the tibia. This tibial member may be provided as part of a dynamic knee balancing system or may be an off-the-shelf tibial trial insert, in various embodiments. In different embodiments, the tibial member may be placed before the femoral member or vice versa. In one embodiment, the femoral and tibial members are engaged with the femur and tibia while the knee is in full or nearly full extension, though in alternative embodiments they may be placed in flexion. The height, thickness, or overall shape of the tibial member may often be selected to provide a desired amount and balance of ligament tension while the knee is in extension.

Generally, the knee is then moved from extension to flexion, and the femoral member is adjusted to adjust tension in the MCL, LCL, posterior cruciate ligament and/or other ligaments to achieve a desired ligament balance in flexion. The knee may then be moved through a range of motion, and one or more subsequent adjustments may be made to the femoral member to adjust and balance ligament tension through the range of motion. Most, if not all, such adjustments and movements may, in some embodiments, be possible while the patella of the knee remains in approximately its normal anatomical position over the knee. This is advantageous because patellar tracking, an important determinant of knee function, may be assessed and adjusted during the TKA procedure. Typically, the goal of the surgeon will be to achieve dynamic balancing of ligament tension through the range of motion of the knee. Once this balancing is achieved with the femoral and tibial members in place, the positioning feature(s) on the adjustable femoral member provide positional information to a surgeon, computer, robotic system and/or the like, to help facilitate completion of the TKA procedure. Using this positional information, subsequent cuts (or drilling, burring or other shaping methods) are applied to the femur, with such cuts/shaping determining how the femoral prosthetic component of the artificial knee joint will be positioned and oriented on the distal femur. The femoral prosthetic component is then placed accordingly.

Figure 5:
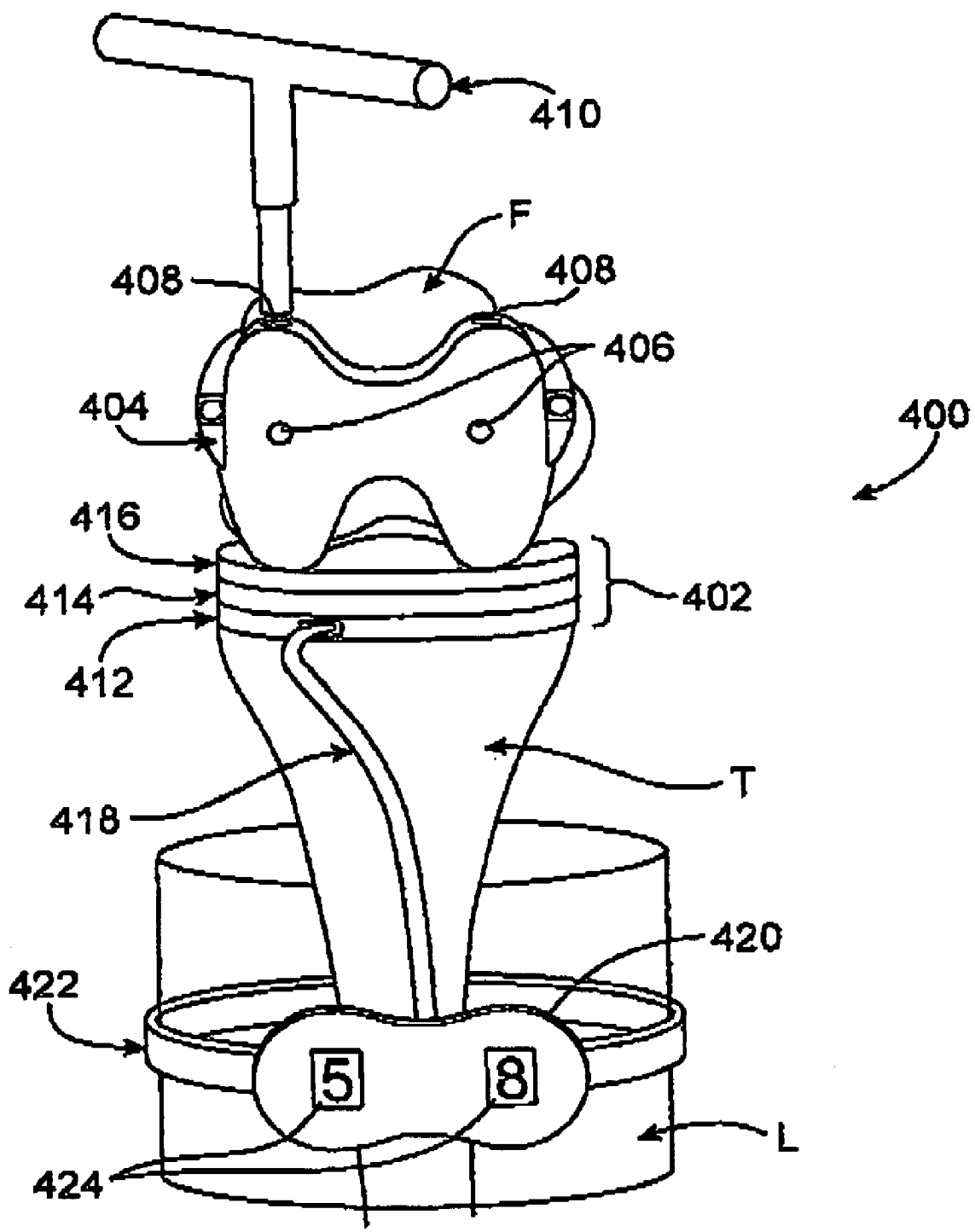
FIG. 5 is a front-perspective view of a knee balancing device with sensing capability, including a visual display and shown with an adjustment member for adjusting the femoral portion of the balancing device according to one embodiment of the present invention.

Referring now to FIG. 5, another embodiment of a knee surgery system 400 generally includes a tibial portion 402, an adjustable femoral portion 404, a visual display 420 and an adjustment tool 410 for adjusting femoral portion 404. Tibial portion 402, which is engaged with a proximal end of the tibia T, includes a sensor plate 412, an adaptor 414, and a tibial insert 416. Sensor plate 412 is coupled with visual display 420 via a cord 418. Visual display 420 includes two LED readouts 424 and a strap 422 for removably attaching visual display 420 to a patient's leg L. Femoral portion 402, which is engaged with a distal end of the femur F, includes two adjustment screws 408 and two positioning apertures 406. Aside from the sensing and visual display components and function, the general operation of tibial portion 402 and femoral portion 404 have been described in detail above.

Figure 6:
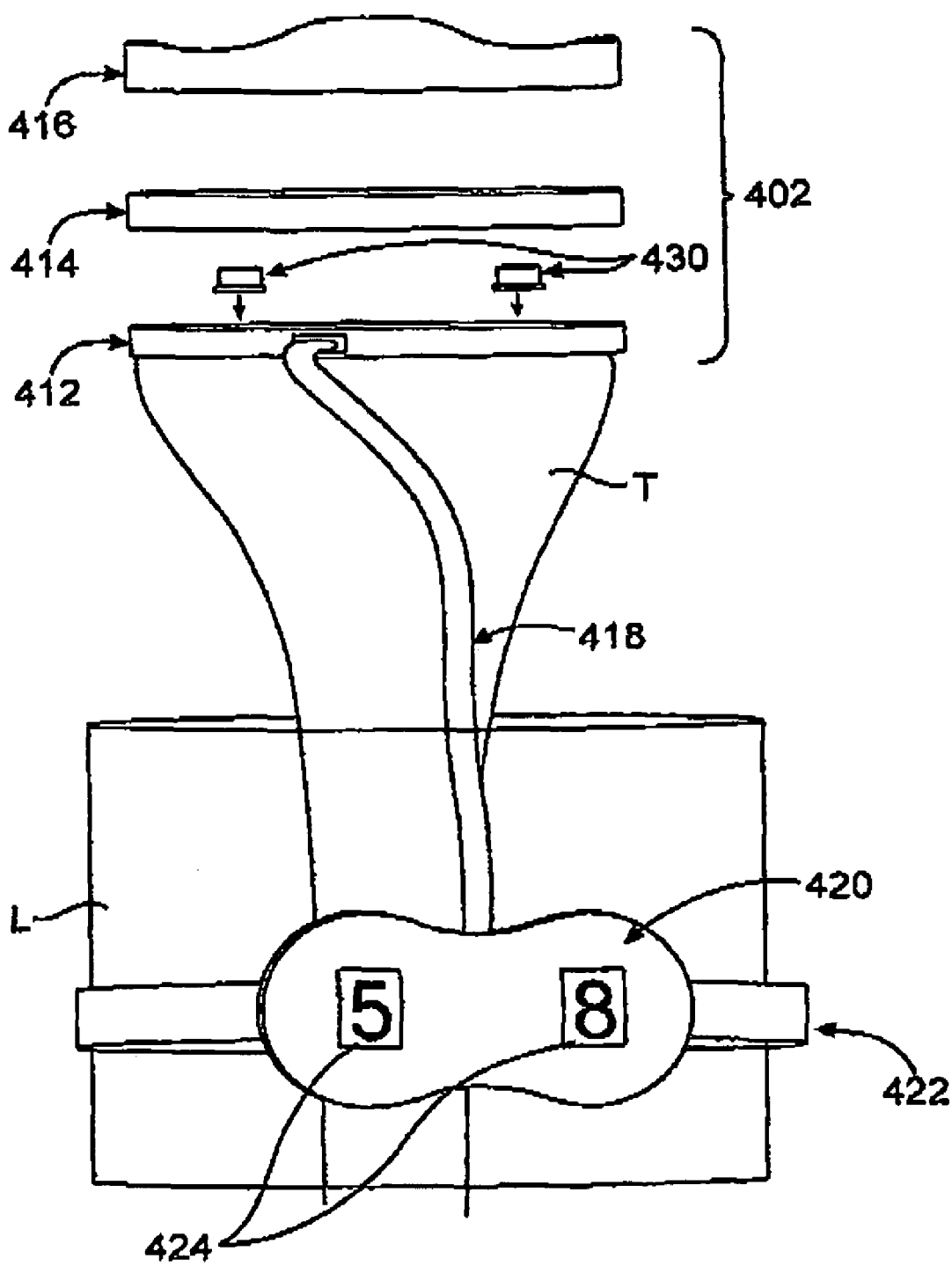
FIG. 6 is a front-perspective view of the tibial portion and visual display of the device of FIG. 5, with the tibial portion shown in exploded view.

With reference to FIG. 6, an exploded view of tibial portion 402 is shown. As illustrated, in some embodiments, sensor plate 412 acts as a housing for one or more sensors 430. Sensors 430 may be any suitable force or pressure sensors, such as but not limited to piezoelectric sensors, force sensing resistors, strain gauges, load cells or the like. In some embodiments, two sensors 430 are used, in order to sense pressure on medial and lateral sides of the knee. In other embodiments, only one sensor 430 may be used, more than two sensors 430 may be used, sensors 430 may be coupled with both tibial portion 402 and femoral portion 404 and/or the like. In one alternative embodiment, for example, sensor plate 412 itself is one large pressure sensor 430, rather than a housing for sensors 430. Any suitable combination, shape, size and configuration of pressure and/or force sensors is contemplated.

Adaptor 414 is generally a plate coupled with sensor plate 412 and adapted to couple sensor plate 412 with tibial insert 416. Typically, adaptor plate 414 is removably couplable with tibial insert 416, such that multiple, differently-sized inserts 416 may be tried in the knee during a surgical procedure, while using the same sensor plate 412 and adaptor 414. In some embodiments, such as the one shown in FIG. 6, adaptor 414 and sensor plate are two pieces attached together. In alternative embodiments, a one-piece plate may be used to house sensors 430 and to couple with tibial inserts 416. In yet another embodiment, all of tibial portion 402 may be one piece. Furthermore, it is not required that sensor plate 412 be located in contact with the tibia T. In an alternative embodiment, for example, sensor plate 412 may be disposed within a tibial insert 416 so as not to contact the tibia T. In the embodiment shown, sensors 430 are embedded in sensor plate 412, and adaptor 414 is attached to sensor plate 412 via adhesive, welding or any other suitable method.

As previously mentioned, sensors 430 may comprise any of a number of suitable pressure and/or force sensors. In one embodiment, a known voltage is transmitted to sensors 430, the voltage passing out of sensors 430 is measured, and a percentage of the voltage leaving sensors 430 to the known voltage is calculated. From this percentage, pressure is derived. An analog signal representing the pressure is converted to a digital signal with an analog-to-digital (A/D) converter, and the A/D converter provides the digital signal to a look-up table that determines a display value (or values) representing the pressure (or force). A user may use the display value as an absolute number and/or may move the knee and compare pressure values at flexion and extension. The A/D converter, as well as any additional processing modules for processing sensed data into usable data may all be housed in a processor (not shown). The processor, in turn, may be housed in sensor plate 412 or in visual display 420. Alternative methods for sensing and displaying sensed data are also contemplated.

Sensor plate 412 is coupled with visual display 420 via cord 418, or alternatively via one or more other connection devices. In alternative embodiments, for example, sensor plate 412 may be coupled with visual display 420 via wireless infrared, electromagnetic, Rf (e.g., using a Bluetooth protocol), optical or other remote, wireless connection(s). In various embodiments, sensors 430 themselves may be coupled with visual display 420, or alternatively, sensors may be coupled with a processor housed in sensor plate 412, and the processor (not shown) may then be coupled with visual display 420 via cord 418 or other means. Visual display 420 itself may be attached directly to sensor plate 412 or may be separate from sensor plate 412, as shown. In various embodiments, visual display 420 may be coupled with the lower leg L or the thigh (not shown) of a patient via a strap 422 or other coupling means. As stated previously, visual display 420 may include a processor for processing sensed data transmitted from sensors 430 into usable data for displaying on LED readouts 424 or other display means.

Figure 7:
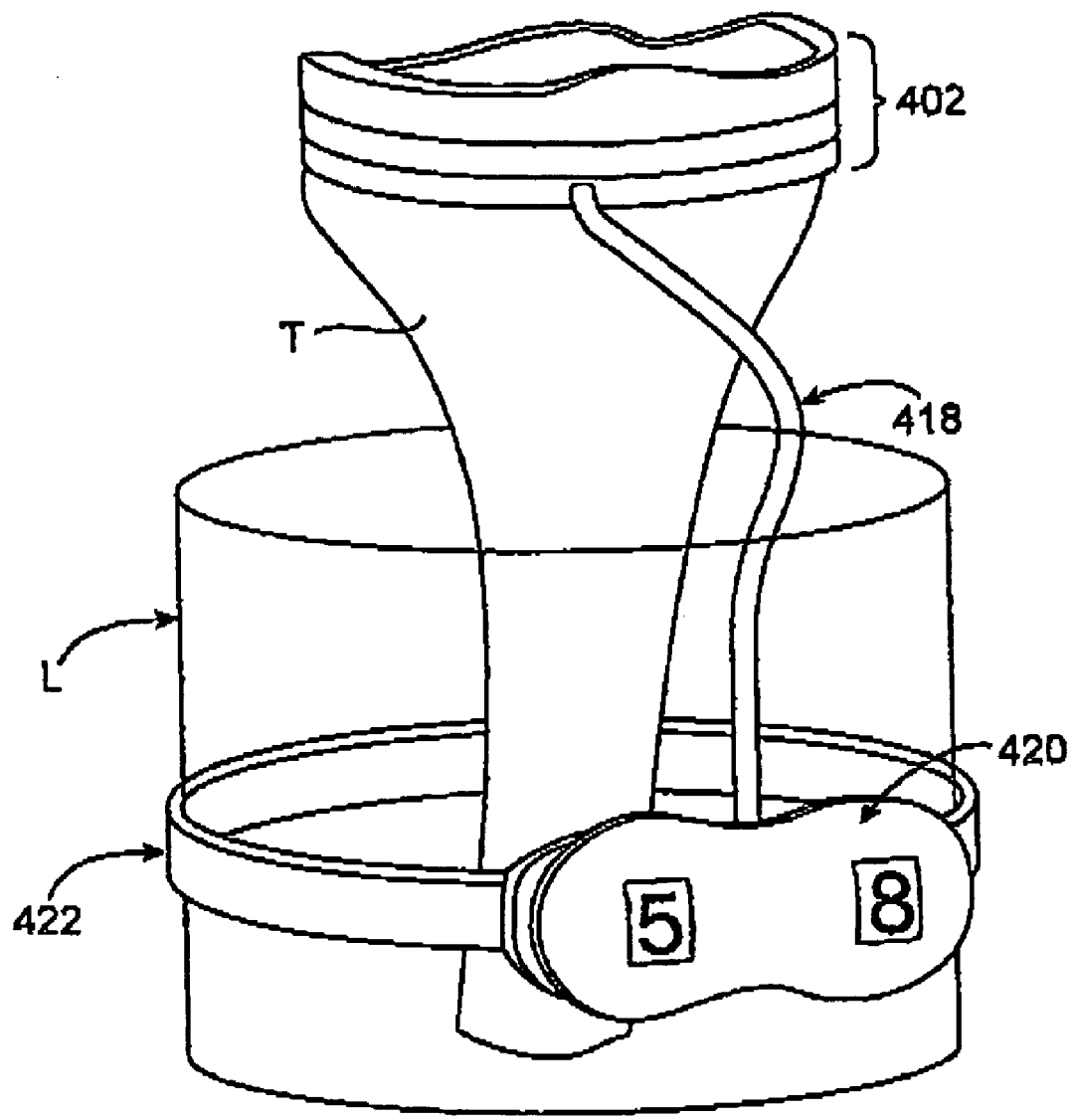
FIG. 7 is a superior, angled perspective view of the tibial portion and visual display of FIGS. 5 and 6.

FIG. 7 is an angled, perspective view of tibial portion 402 and other tibial components of system 400, as in FIGS. 5 and 6.

Figure 8:
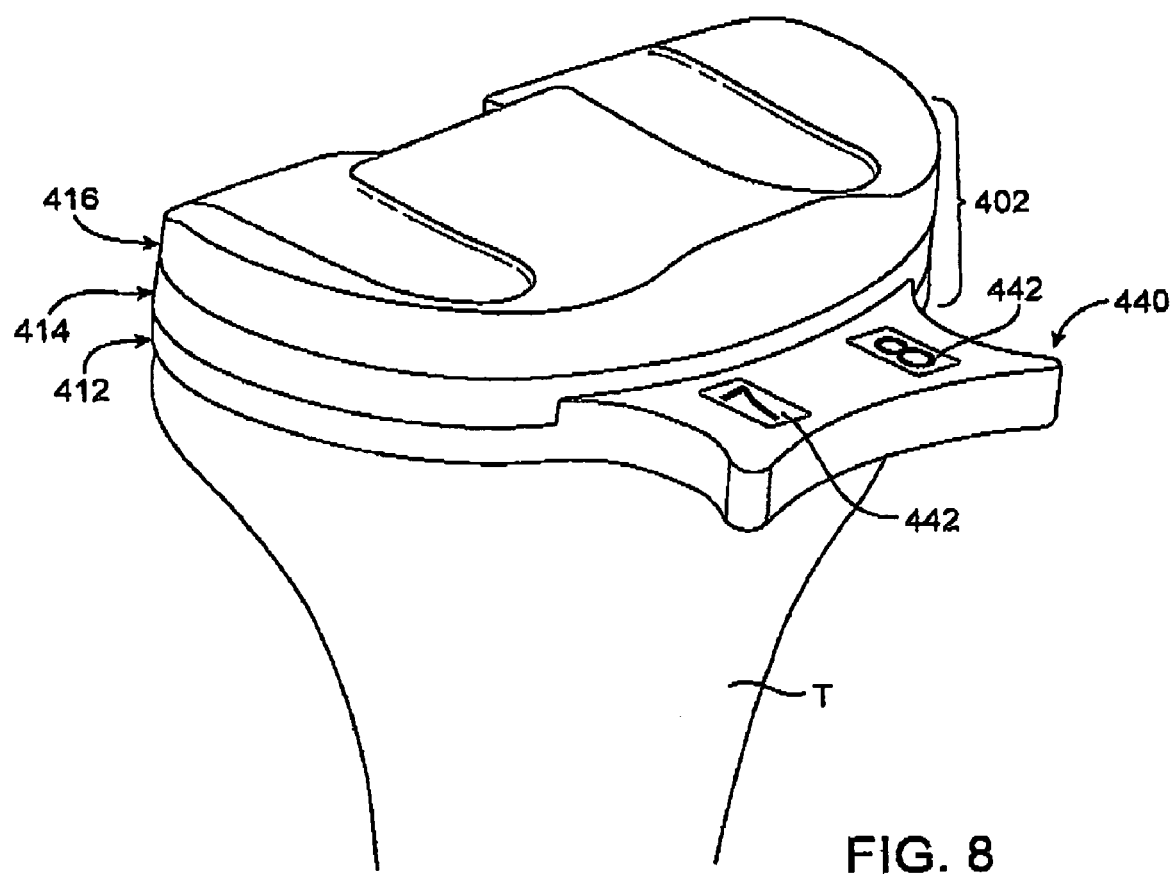
FIG. 8 is a perspective view of a tibial portion of a knee balancing device with sensing capability coupled with a visual display according to an alternative embodiment of the invention.

An alternative embodiment is shown in FIG. 8. As illustrated, tibial portion 402 may in some embodiments be attached to an immediately adjacent visual display 440 having multiple LED readouts. Either the sensors, the processor (neither are visible) or both are coupled with visual display 440. In some embodiments, visual display 440 is coupled with both sensor plate 412 and adaptor 414. Visual display 440 may have any suitable size, shape and overall configuration and may be positioned in any appropriate location, relative to the rest of system 400.

Figure 9:
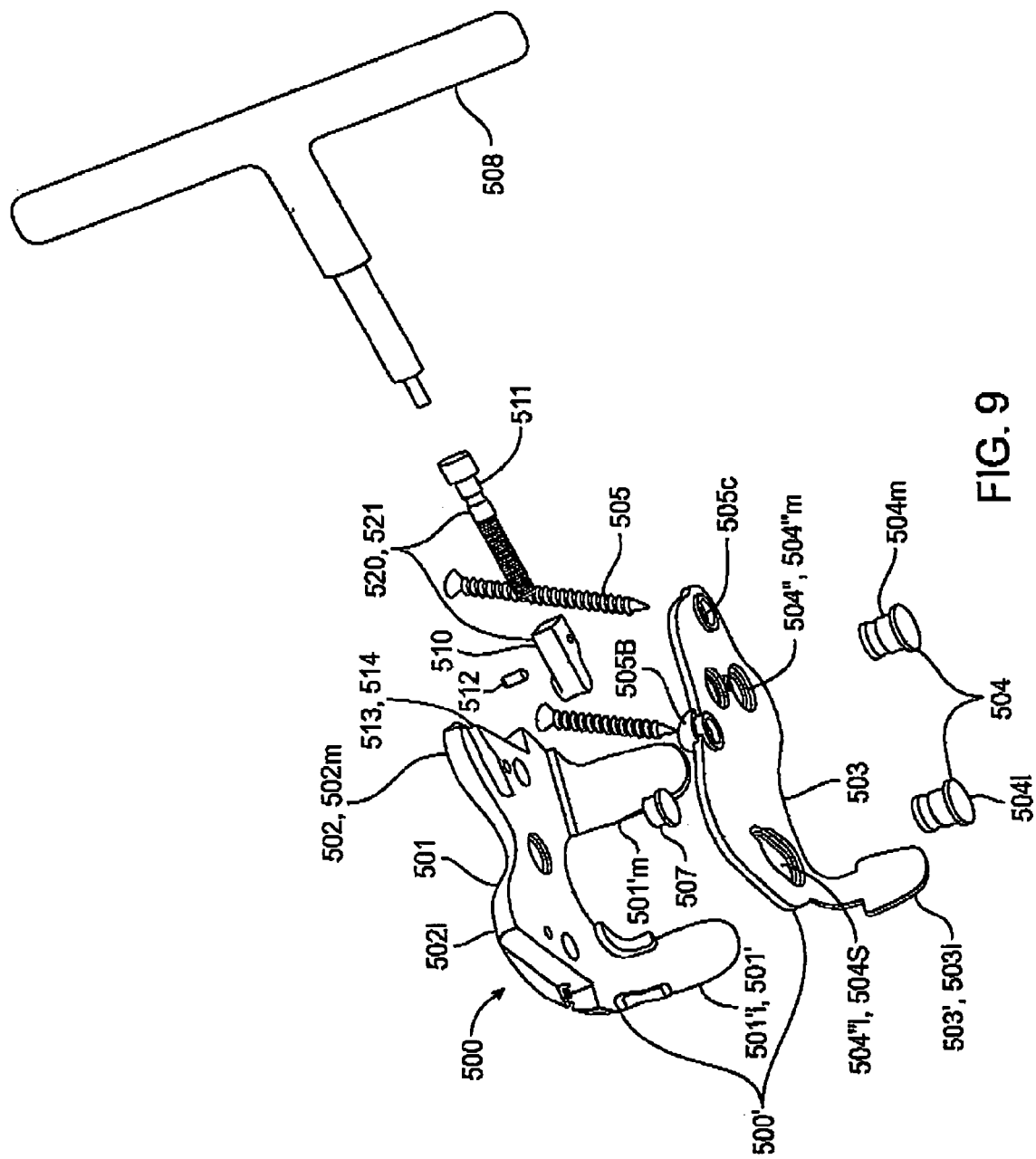
FIG. 9 is an exploded view illustrating an embodiment of a dynamic knee balancing device having an opposing adjustment mechanism.
Figure 10A:
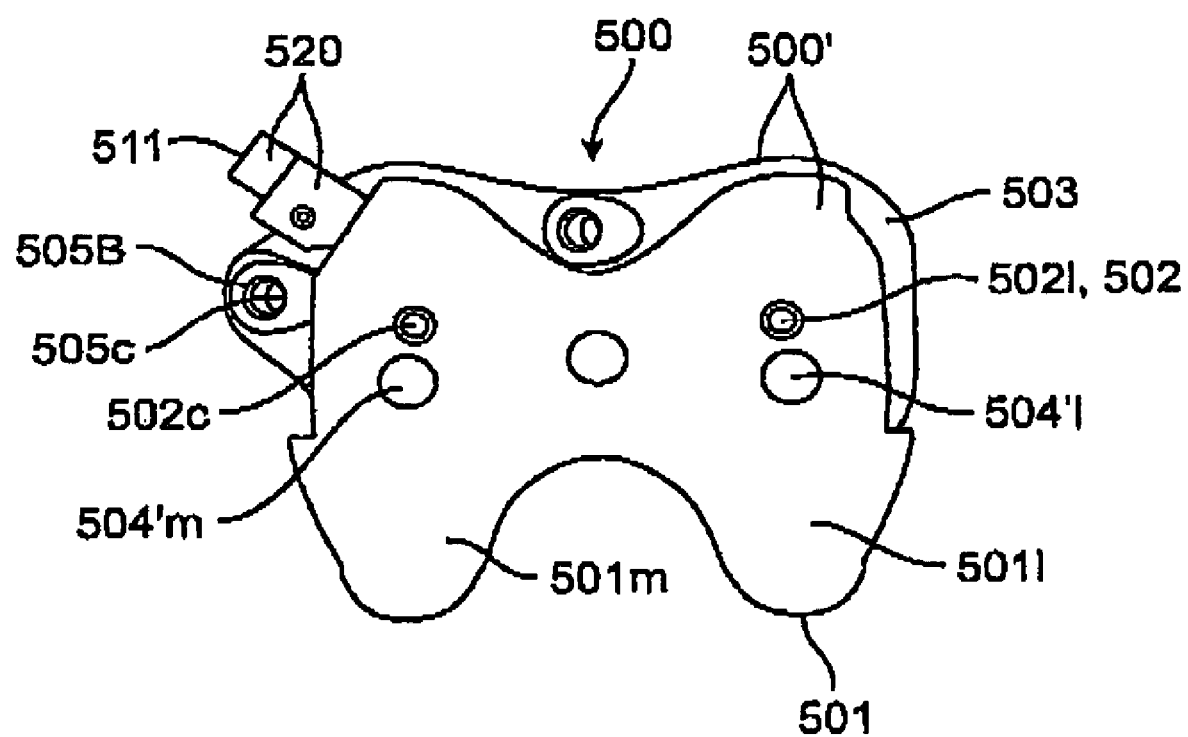
FIGS. 10A and 10B is are frontal (10A) and back (10B) views of the embodiment of FIG. 9.
Figure 10B:
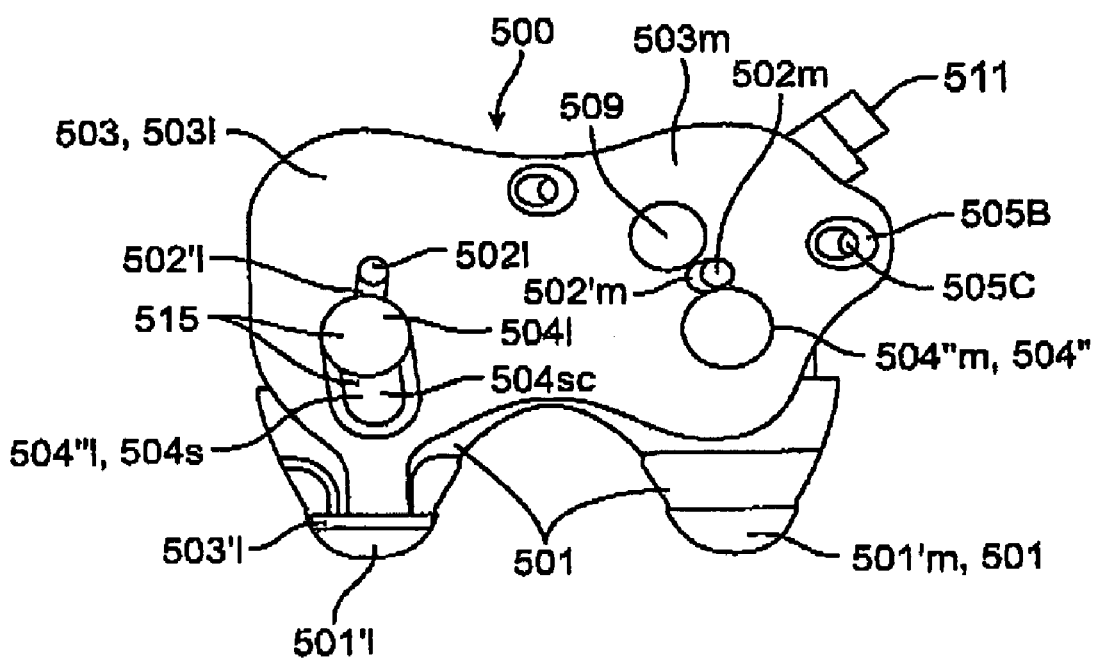
Figure 11:
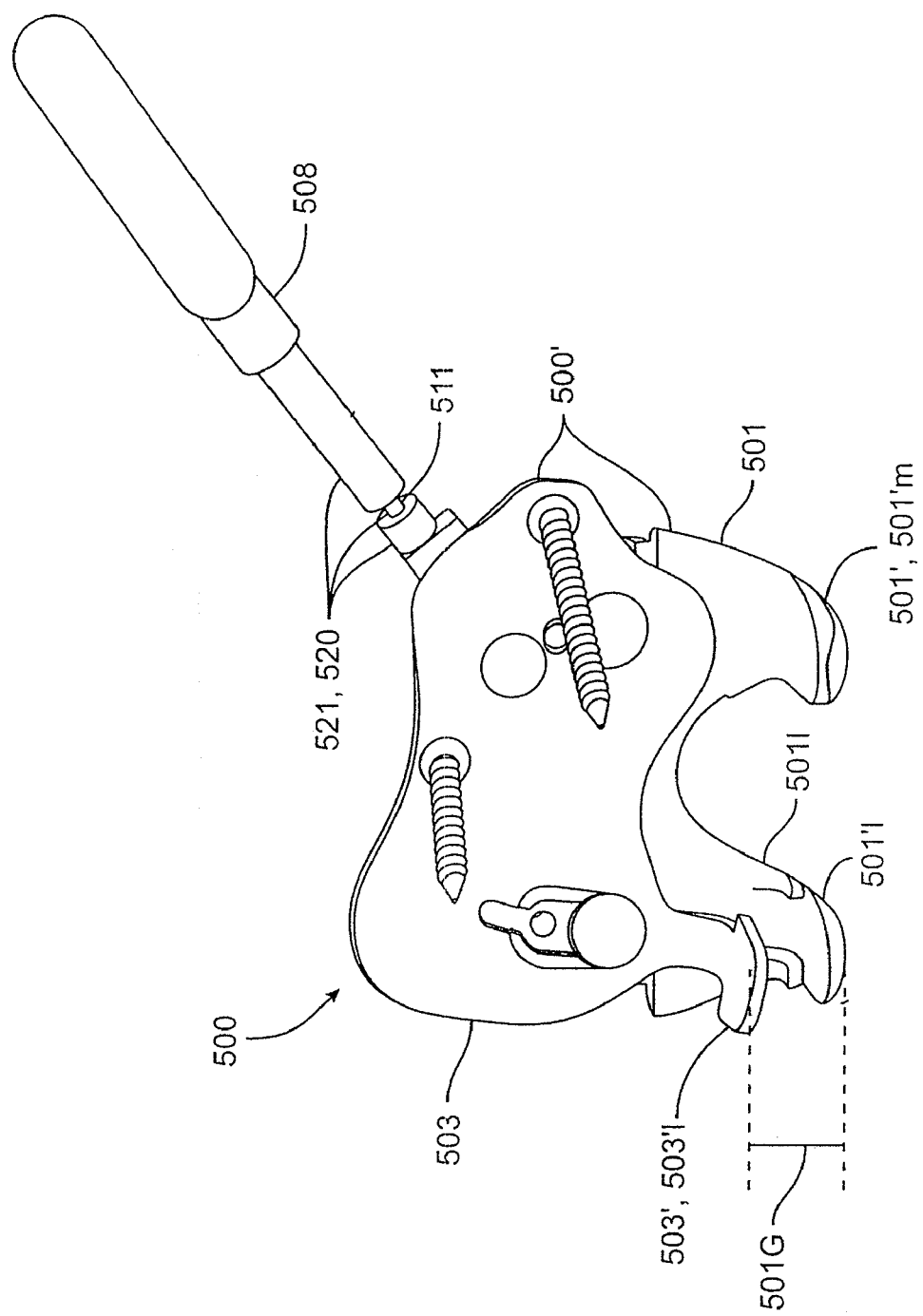
FIG. 11 is a perspective view illustrating the operation of the mechanism of the embodiment of FIGS. 9 and 10.

Referring now to FIGS. 9-11, an embodiment of a dynamically knee balancing device 500 having an opposing adjustment mechanism 520 will now be discussed. The device includes a femoral assembly 500' having an adjustable femoral member 501 having lateral and medial portions 501l and 501m and a stationary femoral member 503 having lateral and medial portions 503l and 503m. The two are pivotally coupled by pivot bushings or other pivotal couplings 504 which fit through medial and lateral clearance openings 504' on members 501 and medial and lateral openings 504" on members 503. Adjustable member 501 includes apertures 502 which operate as positioning features as described herein. Respective lateral and medial apertures 502l and 502m are substantially aligned with lateral and medial clearance openings 502l' and 502'm such that when member 501 rotates the apertures allow access to the distal femur through openings 502l' and 502'm. Fixation screws 505 are used to reversibly fix the stationary member 503 to cut sections of the distal femur as described above. Fixation screws 505 are advanced through fixation holes 505C and through fixation bushings 505B mounted to stationary member 503. Bushings 505B can be angled to produce an angled entry of the screws into the bone. Bushing 505B serve to providing structural support and rigidity to the stationary member to help distribute the forces exerted by the screws onto the member. This in turn helps to set the screws into the bone by allowing the screws to tightened with greater amounts of torque. Member 501 can also include an identification feature or button 507 which fits in identification feature hole 507A. Identification feature can include markings identifying device 500, (e.g., a color button indicating size, a bar code indicating model and lot #) as well as Rf (e.g. using Bluetooth protocol) or other wireless identification device.

Stationary femoral member 503 can include one or more stationary posterior condylar members 503'. Similarly, adjustable femoral member 501 suitably includes one or more (preferably two) adjustable posterior condylar members 501' extending posteriorly to emulate the two posterior condyles PC. In a preferred embodiment, adjustable member 501 includes two posterior condylar members 501' lateral (501'l) and medially (501'm) positioned and stationary member 501 includes one posterior condylar member 503' positioned on a lateral portion 503l of member 503. In the preferred embodiment, the lateral condylar members 501'l is adjustable and the lateral member 501'm is not in that it acts a fulcrum. Preferably, condylar member 503' substantially aligns with and flushably engages lateral condylar member 501'l when member 501 is an un-rotated position with respect to member 503 (See FIG. 10B). However in alternative embodiments, there can be an offset between the aforementioned condylar members in the un-rotated state and they need not be aligned. As is described herein, posterior condylar members 501', 503' allow femoral member/assembly 500' to be adjusted to balance ligament tension in the knee K and also allow knee balancing system 500 to remain in place within the joint space while the knee K is moved through a range of motion. In various embodiments, stationary femoral member 503 and stationary posterior condylar members 503' may be either multiple, coupled parts or may be one piece (e.g. a cast or molded component). Similarly, adjustable femoral member 501 and adjustable posterior condylar members 501' are all one piece in some embodiments, but may alternatively comprise multiple coupled parts.

The position of adjustable member 501 is adjusted relative to stationary member using a mechanism 520. In the embodiment shown, mechanism 520 is configured to rotably adjust member 501 relative to stationary member 503, but in various embodiments, it can be configured to adjust member 501 by vertical or horizontal translation or a combination of both. Mechanism 520 is operated by means of an actuator 511 configured to by engaged by adjustment device 508. In a preferred embodiments actuator 511 is an adjustment screw and adjustment device 508 is a hand held tool such as a T-wrench. Other actuators can include pins, bolts, knobs, ratchets, rocker arms and the like. Other adjustment devices can include screw drivers, Allen wrenches and the like. Screw 511 engages a pivot guide or cam 510 which fits within a guide recess 513 within member 501. When turned, adjustment screw 511 engages pivot nut 509 to exert a force on member 501 causing it to pivot. Screw 511 can be held in place with a lock pin 512. Rotational movement is achieved by configuring clearance opening 504"m as a substantially round hole and opening 504"l as a curvilinear or linear slot 504s such that medial bushing 504m in opening 504"m can only rotate while the lateral pivot bushing 504l in opening 504"l moves in one or two dimensions. The amount of rotational movement of member 501 can be controlled by selecting the length and dimensions of slot 504s relative to lateral bushing 504L such that slot 504s acts as a stop 515 to lateral bushing 504L and vice versa. Also the central axis 504sc of slot 504s is aligned with lateral aperture 502l such that the two openings (504l and 502l) overlap through the range of adjustable motion of member 501 by mechanism 520 (See FIG. 10B). In other words, access through opening 502l to the femur remains unobstructed through the range of motion of member 501.

FIG. 11 illustrates the operation of an embodiment of mechanism 520 in adjusting adjustable member 501. As the figures show, turning of a medial side mounted actuator 511 (with respect to member 501) by adjustment device 508 (in this case a wrench), causes the lateral portion 501l of adjustable member 501 to rotate relative to stationary member such the opposite or lateral posterior condylar member 501'l is raised or lowered with respect to lateral posterior condylar member 503'l to produce a desire gap or spacing 501G between the two respective posterior condylar members. As discussed herein, the range of motion of mechanism 520, and thus the maximum amount of gap 501G can be controlled by means of a stop 515. In various embodiments, mechanism 520 can configured to produce an adjustable gap 501G ranging from 0 to 20 mm, with specific embodiment of 5, 10 and 15 mm. In other embodiments, mechanism 520 can be configured to produce a selectable gap 501G through vertical and/or horizontal adjustment of member 501 with respect to member 503

Embodiments of mechanism 520 can be configured to provide a number of operational features to balancing device 500. In particular, by having the actuator mounted on the opposing side of the device that is adjusted the mechanism allows adjustment to adjustable member through the full range of motion of the knee. This in turn, allows ligament tension to be balanced through the full range of motion to provide for dynamic balancing of the knee. Further, embodiments with side mounting of the actuator allow the surgeon to both observe and access the joint space including the spacing between the adjustable femoral member and the tibial member (described herein) while the knee is moved through its full range of motion without substantial physical or visual obstruction of the surgical site by one or more of the actuator or actuation device. This in turn allows for a more uniform balancing of the knee through its range of motion by allowing the surgeon to move the knee through its range of motion with one hand while making adjustments with the other. Further, the surgeon can continuously adjust and observe the fit of the adjustable member to the tibial member and the balance of the knee while moving the knee, instead of having to make an adjustment and then observe the fit. Such one handed operation can be facilitated by configuring mechanism 520 such that actuator 511 can be readily turned from the torque of the unaided fingers or that from a handheld adjustment device 508. Also, as discussed above, these and related embodiments allow adjustment to the adjustable member to dynamically balance the knee without eversion or substantial displacement of the patella tendon.

Mechanism 520 operates as one form of an adjustment means 521 for adjusting adjustable member 501. Other adjustment means 521 that can be employed can include without limitation, cam mechanisms, geared mechanisms and electromagnetic mechanisms, hydraulic mechanisms and pneumatic mechanisms. Such mechanisms can be configured to allow the surgeon to continuously adjust adjustable member by means of a foot pedal or other remote actuation device while the knee is extended through its range of motion.

Figure 12A:
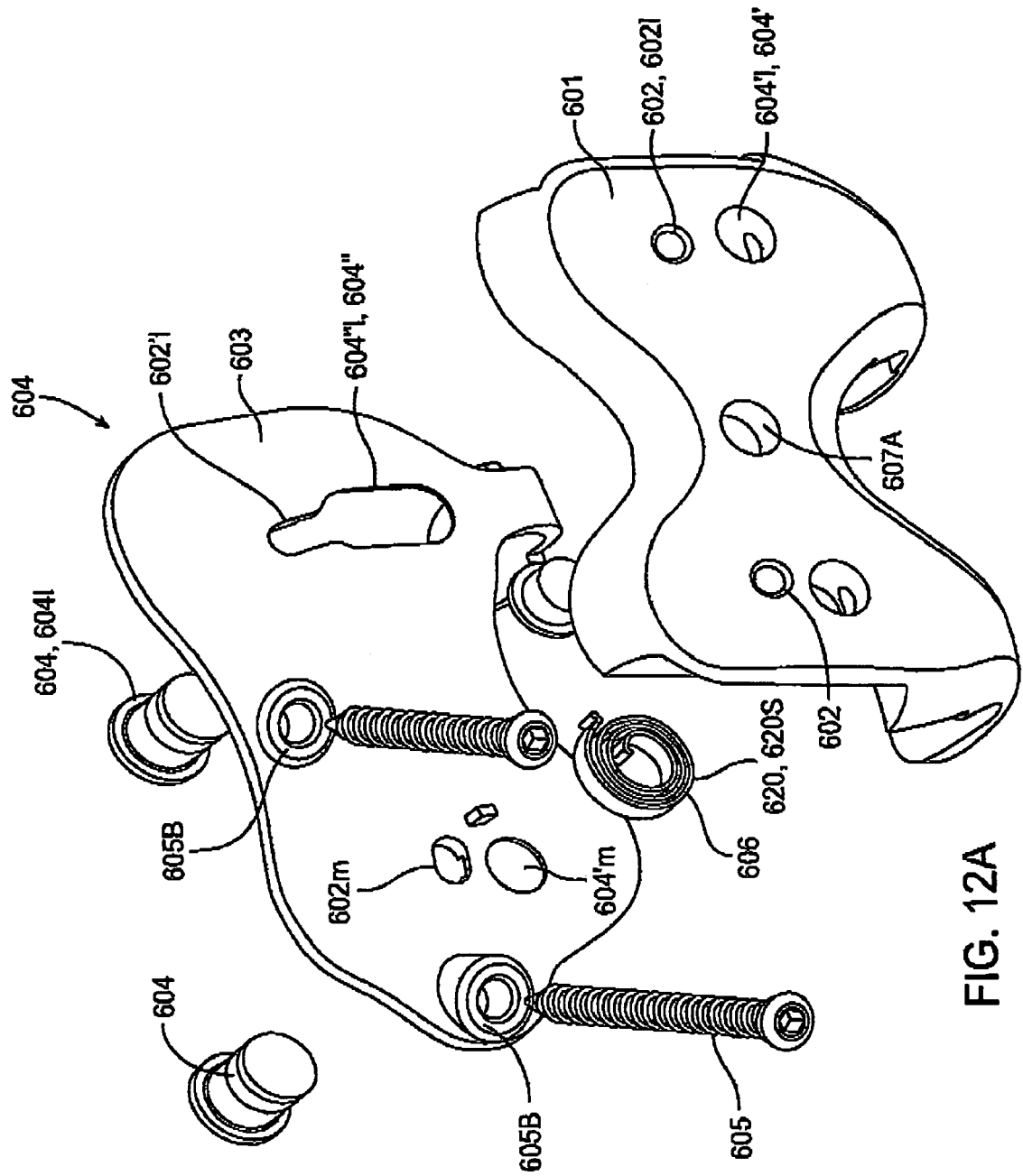
FIGS. 12A and 12B are perspective views illustrating embodiments of a self-adjusting knee balancing device.
Figure 12B:
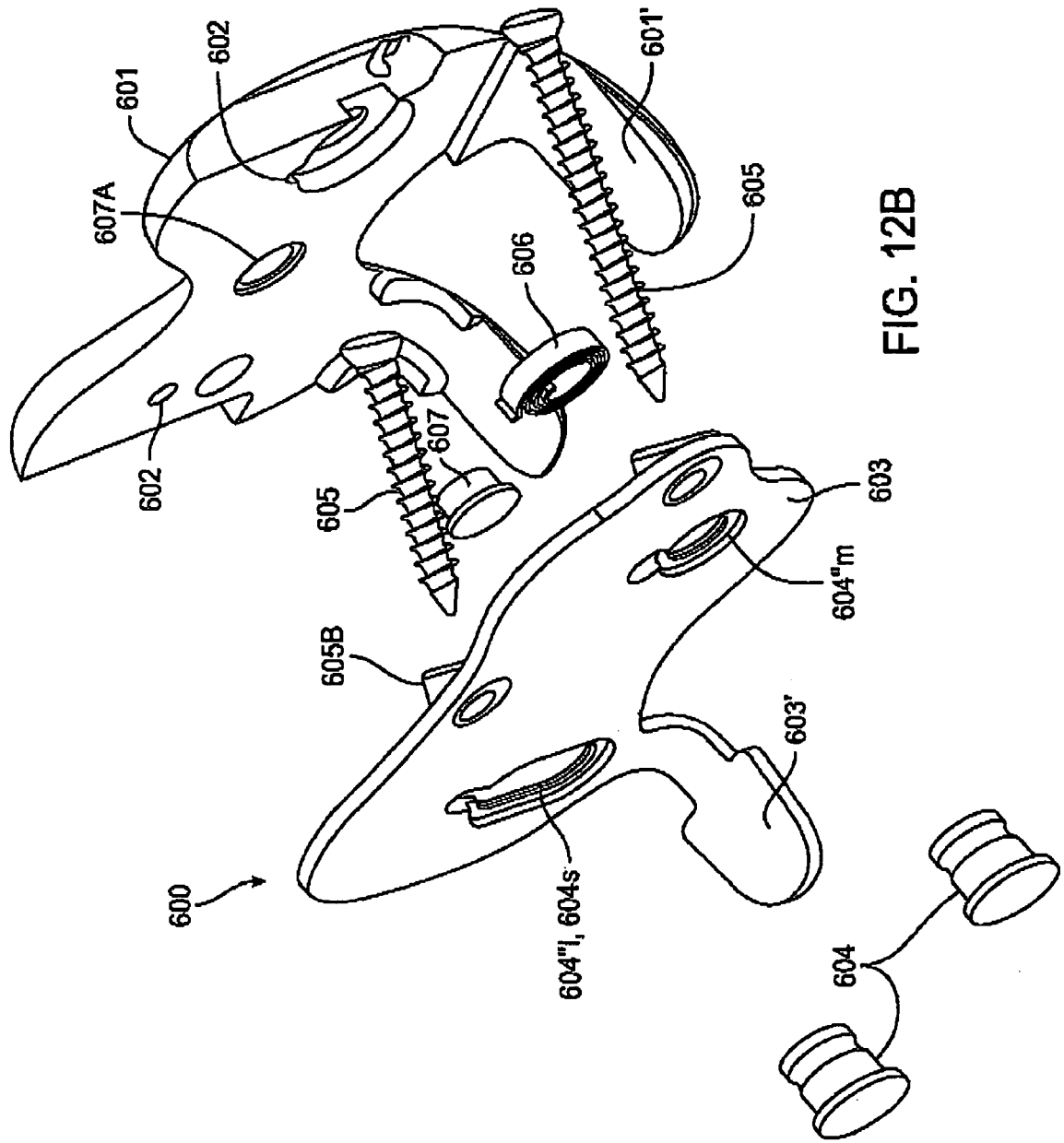
Figure 13:
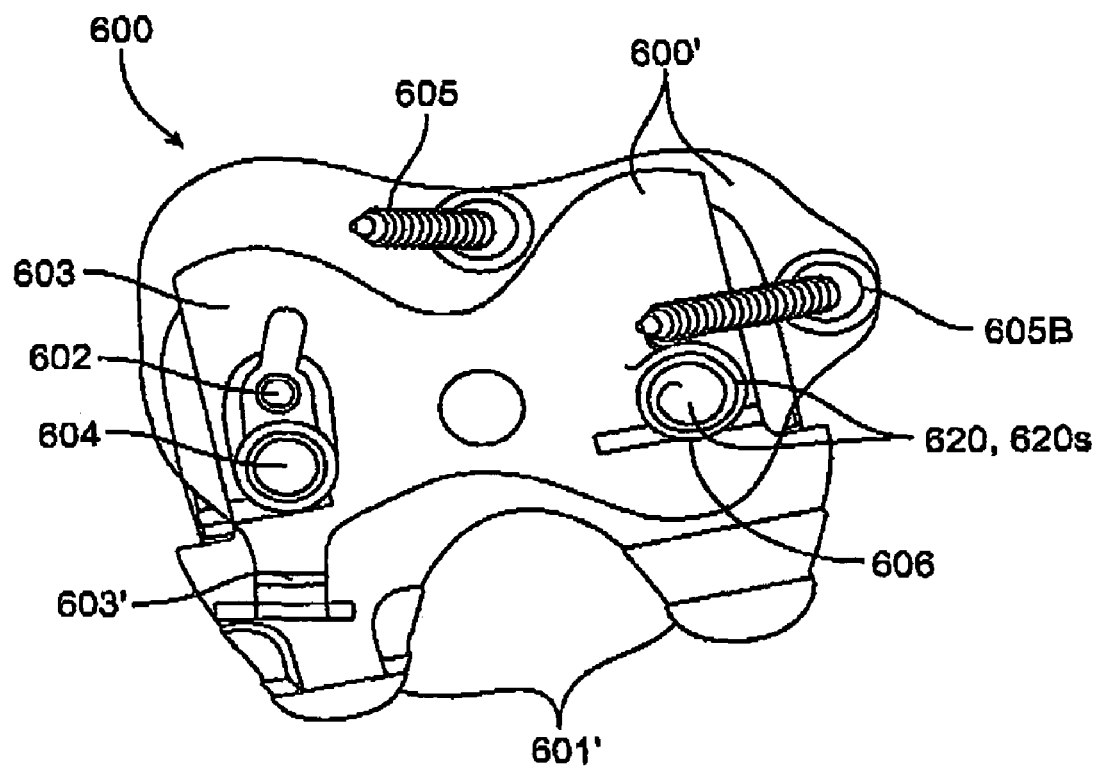
FIG. 13 is a phantom view of a self adjusting balancing device.

Referring now to FIGS. 12-13, a discussion will now be presented of a self-adjusting knee balancing/prosthetic device 600. As shown in FIG. 12A-12B, device 600 includes a femoral assembly 600' including an adjustable member 601 and stationary member 603. Also as shown in the figures, many of the components and features of device 600 are substantially the same or similar to those on device 500 including for example opening 602, bushings 604, screws 605, screw bushings 605B, and assorted openings etc (the numbers for other components in system 600 correspond to the 500 series numbers for system 500). However, the adjustment mechanism 520 now comprises a self adjusting mechanism 620 that is configured to self adjust responsive to the tension or force exerted by one or more tendons or ligaments adjacent the knee so as to dynamically balance the knee through its range of motion as described herein. More specifically, adjustment mechanism 620 is configured to adjust the adjustable femoral member 601 relative to member 603 responsive to a tension of the adjacent tendons or ligaments of the knee. Accordingly, mechanism 620 can be coupled to one or both of member 601 and 603.

In various embodiments, self-adjusting mechanism 620 can comprise a spring loaded mechanism 620s including one or more springs 606 or spring like elements known in the art. Suitable springs 606 can include one or more of coil springs, leaf springs, flat springs, clock springs or other spring known in the art. In a preferred embodiment, spring 606 is a clock type spring made from spring steel or other shape memory materials known in the art. As is discussed below, spring 606 is biased to put the tendons or ligaments of or adjacent the knee in tension so as to dynamically balance the knee through its range of motion. Also spring 606 is configured to adjust adjustable member 601 responsive to the tension or force exerted by those tendons or ligaments on one or more of device 600, member 601 or member 603.

In various embodiments, self adjustment mechanism 620, 620s is configured to exert sufficient spring or other force on the tendons/ligaments adjacent the knee to put the tendons/ ligaments in tension. The spring force of mechanism 620 can be selected to put the tendons or ligaments of or adjacent the knee in sufficient tension so as to balance the knee of the individual patient through the range of motion of the knee. Such balancing allows enhancement of one or more of the range of motion, stability or patella tracking of the knee Selection of the appropriate spring force for the knee of a particular patient can be achieved by measurement of the tension of the tendon using force or strain gauges or sensors described herein or known in the art combined with visual observation or measurements of the fit between the adjustable member 601 and tibial members through the range of motion of the knee.

Figure 14:
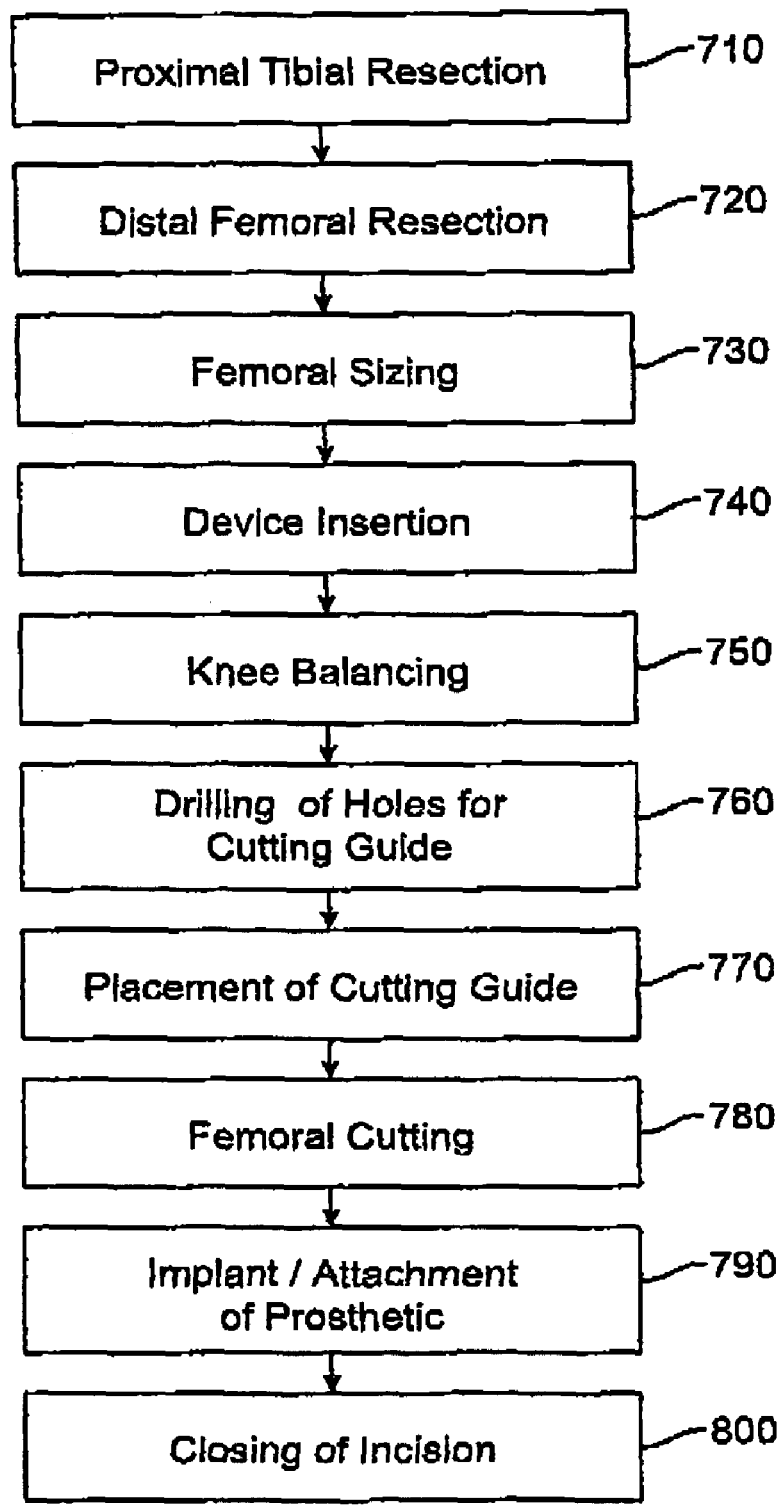
FIG. 14 is a flow chart illustrating an embodiment of a method for using the knee system of the invention for performing minimally invasive TKA surgery on the knee.

Referring now to FIGS. 14 and 15 an embodiment of a method or algorithm 700 for using embodiments of a knee balancing system and device for performing a minimally invasive TKA procedure will now be described. The system 10 can include one or more knee balancing devices described herein including balancing device 500 having an opposing adjustment mechanism described above. The steps and order of this method are exemplary and other order or steps may equally applicable. First a proximal tibial resection step 710 is performed as described above and shown in FIG. 15A. Then a distal femoral resection step 720 is performed described above and shown in FIG. 15B. Next a femoral sizing step 730 is performed as shown in FIG. 15C in order to determine the appropriate size of the components to be selected and used in system 10/device 500, e.g. the femoral adjustable member and stationary members, etc. Once the components for system 10 are selected then femoral assembly 500' is inserted into the surgical incision in an insertion step 740. Typically insertion step 740 will include the attachment of the stationary femoral assembly to the distal femur as described herein. Insertion step 740 can also include insertion of the tibial member 14 such as a tibial shim described herein, or an implantable tibial member can be reversibly attached at that time. Then an adjustment or balancing step 750 is performed (See FIG. 15D) in which a hand held adjustment device such as a wrench is used turn an actuator positioned on one side/ portion of the adjustable member to adjust the opposing side/ portion of the adjustable member. Adjustments are made such that the distance or gap between the tibial and adjustable femoral members is substantially uniform throughout the range of motion of the knee. This can be done by making an adjustment with one hand and then checking the gap while putting the knee through a range of motion with the other hand. In an embodiments of the system having a side mounted actuator, such as an adjustment screw, adjustments are made to one side of the adjustable member, by adjusting the adjustment screw on the opposite side of the adjustable member/ femoral assembly. Typically, the adjustments are made to the lateral side, by adjusting the adjustment screw positioned on the medial side. Alternative embodiments can have the opposite configurations. These and related embodiments allow the knee to be balanced through a full range of motion without requiring the patella to be everted or otherwise displaced in order to gain access to the surgical site of the knee (e.g., the distal femur, proximal tibia, etc). The side mounted actuator also allows the adjustable member to be adjusted and without visual or physical obstruction of the surgical site. This allows the surgeon to continuously observe the balance of the femoral assembly (e.g., the space between the tibial and adjustable femoral members) while making adjustments at any point along the range of motion of the knee. Moreover, these and related embodiments can allow the surgeon to make adjustments to balance the femoral assembly and thus balance ligament tension while the knee is in motion.

In one embodiment of a method for making adjustments to balance the knee, the surgeon will check the gap between the tibial and adjustable femoral members at various points of flexion and extension of the knee and make adjustments as needed to bring the knee in balance throughout the complete range of motion of the knee. Initially, gross adjustments can be made to bring the knee generally in balance by checking the balance at full flexion, full extension and a selected midpoint. Subsequently, finer adjustments can be made by making observations/measurements at multiple locations in the range of motion so as to obtain a more uniform balance throughout the entire range of motion of the knee.

Figure 15A:
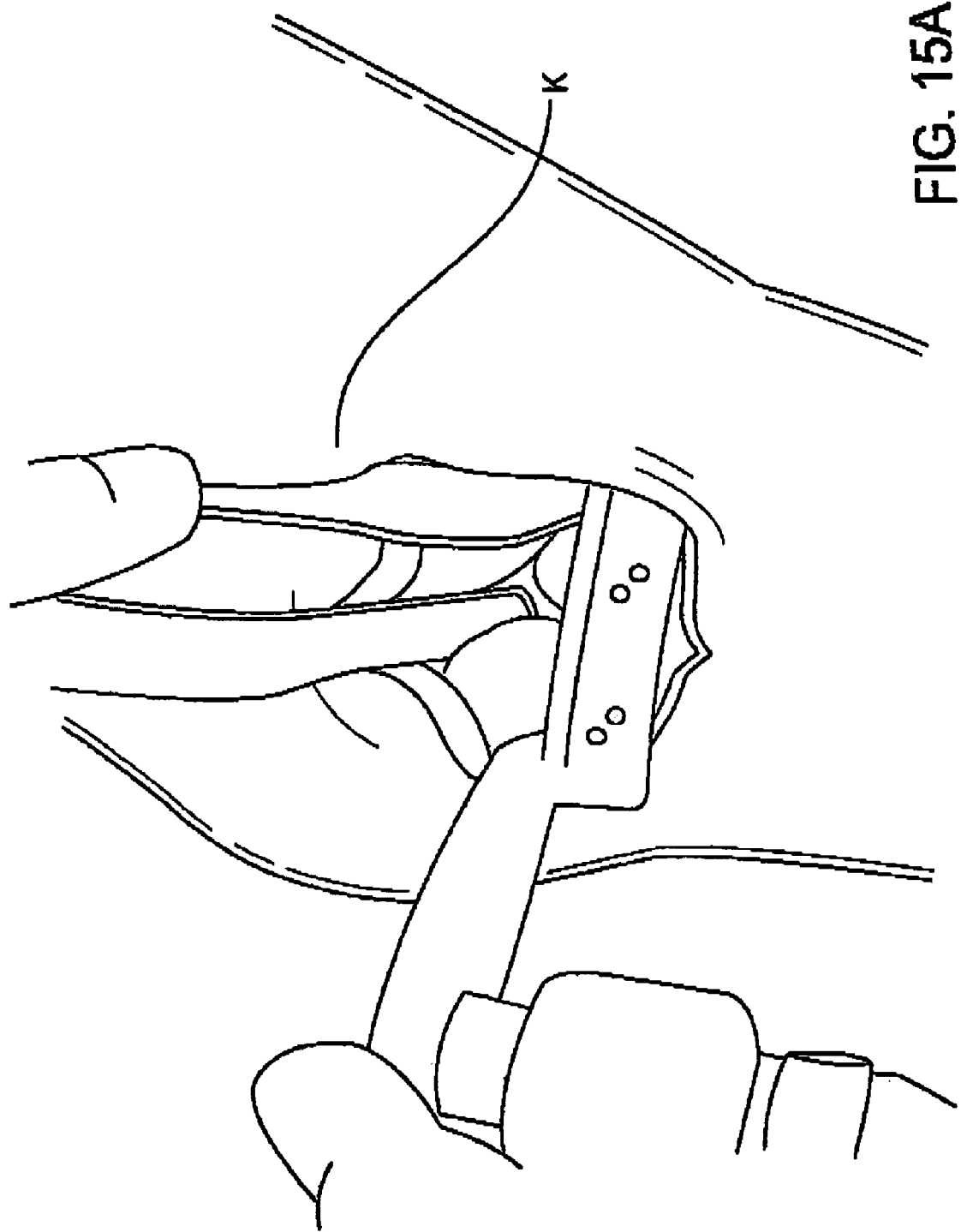
Figure 15B:
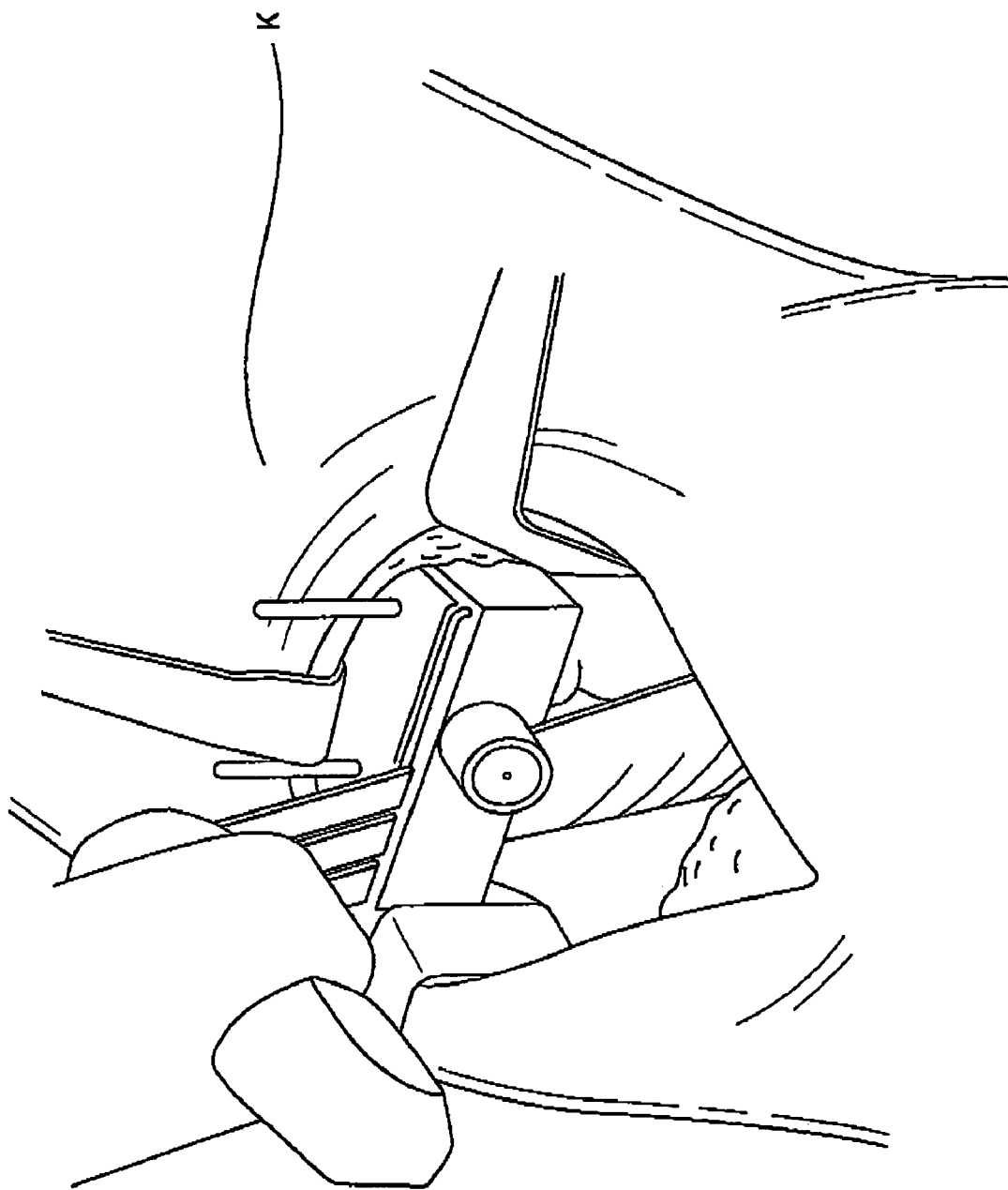
Figure 15C:
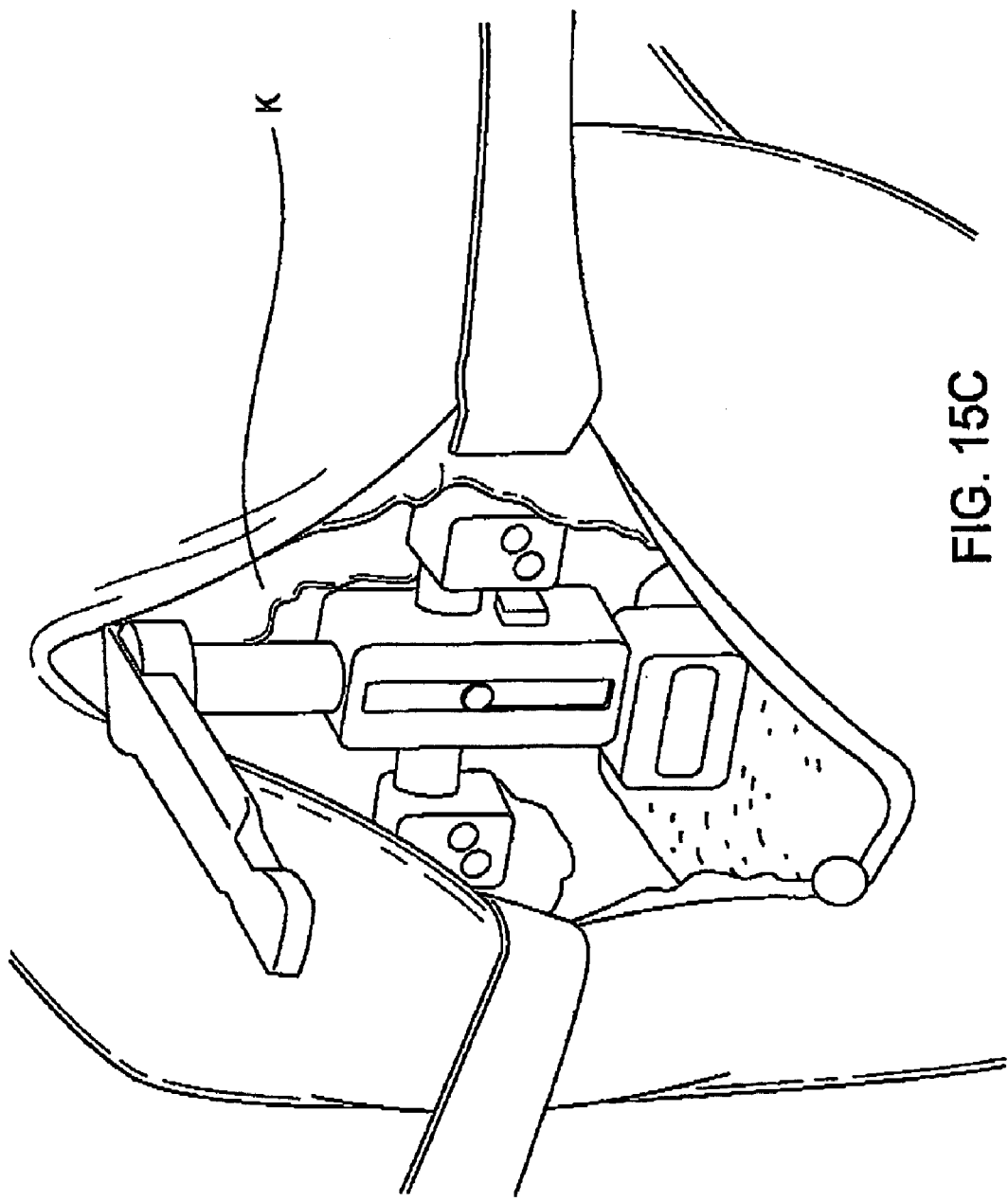
Figure 15E:
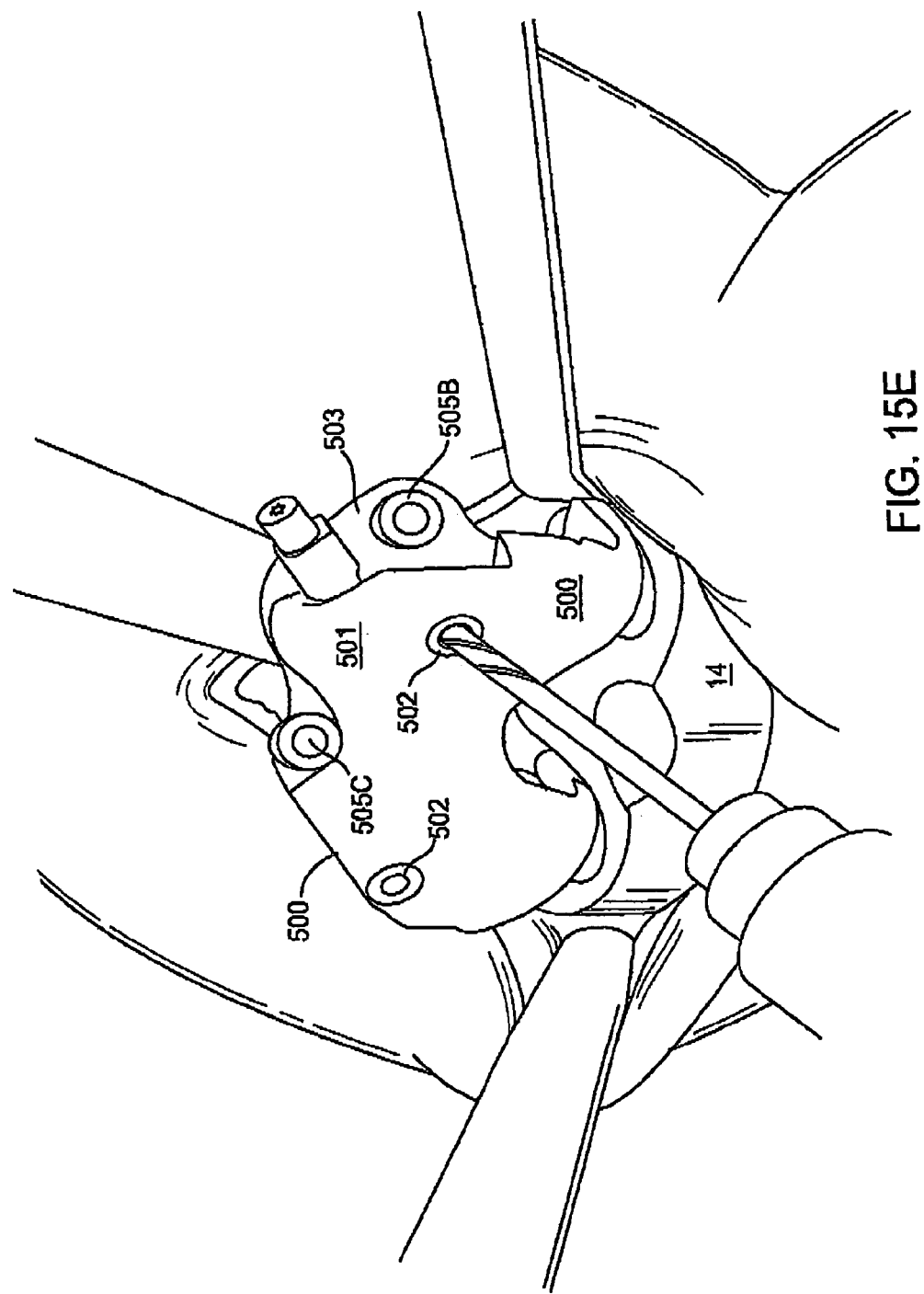
Figure 15F:
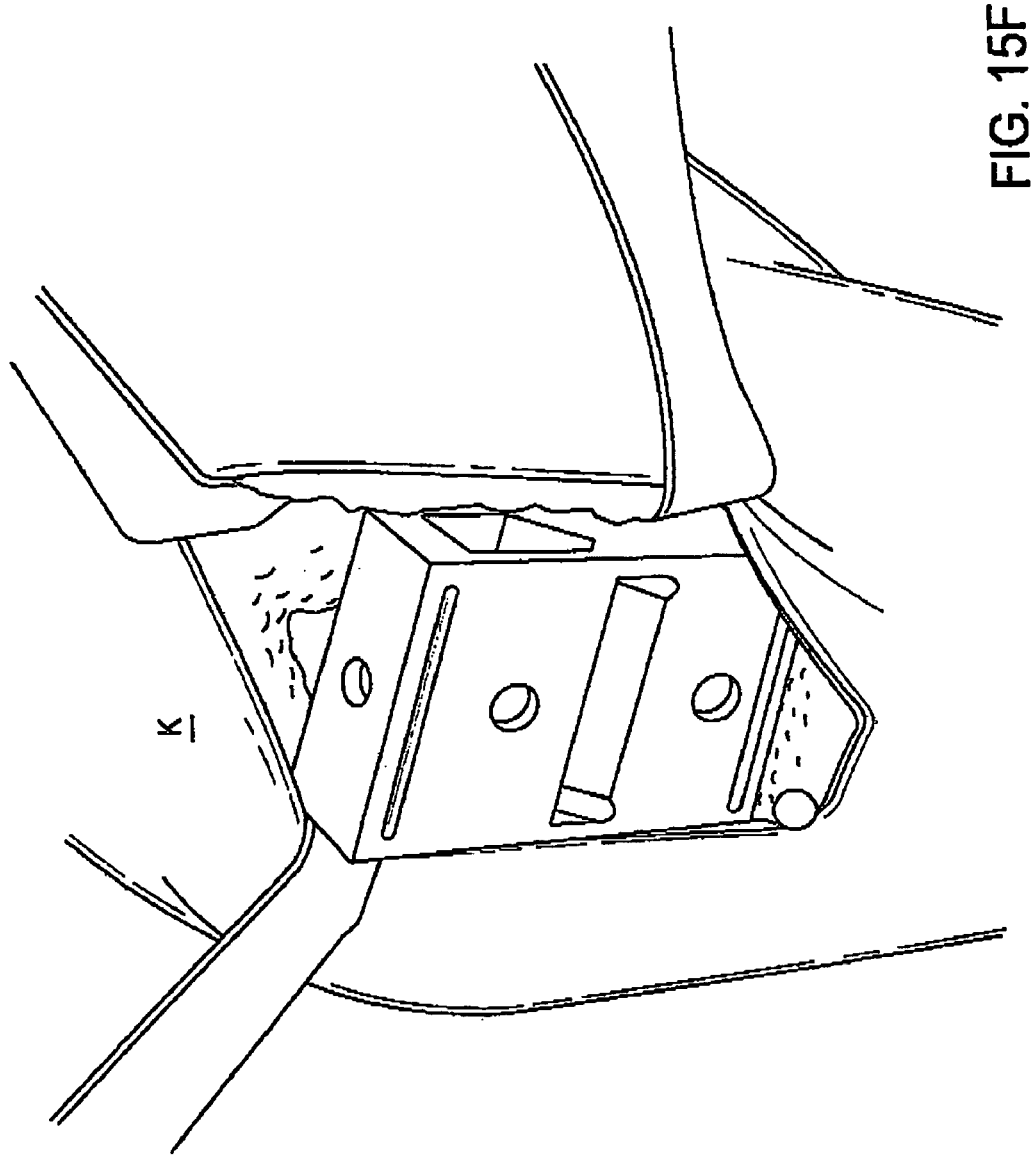
Figure 15G:
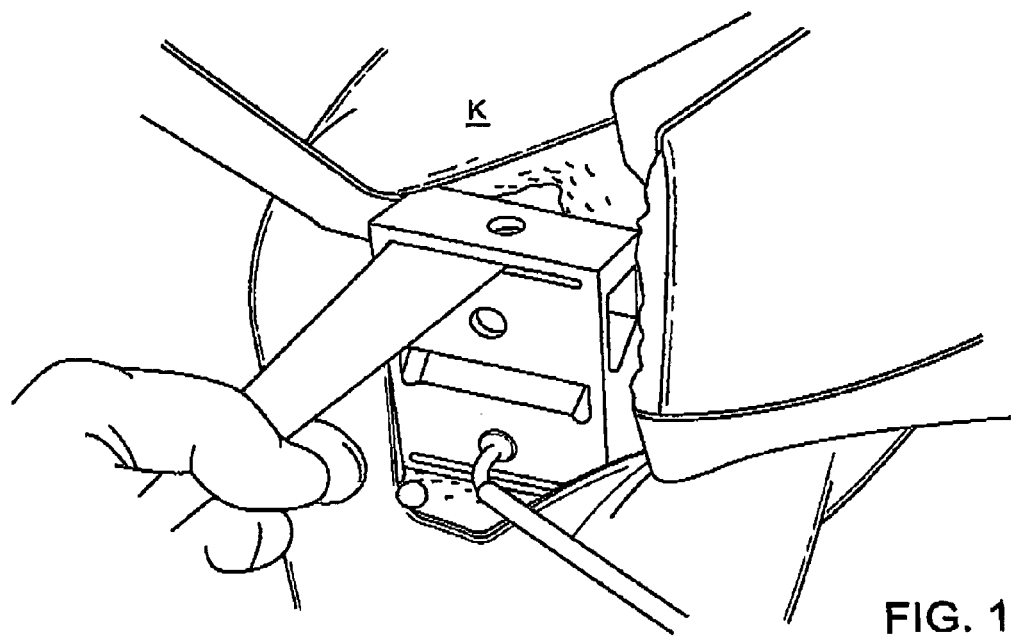
Figure 15H:
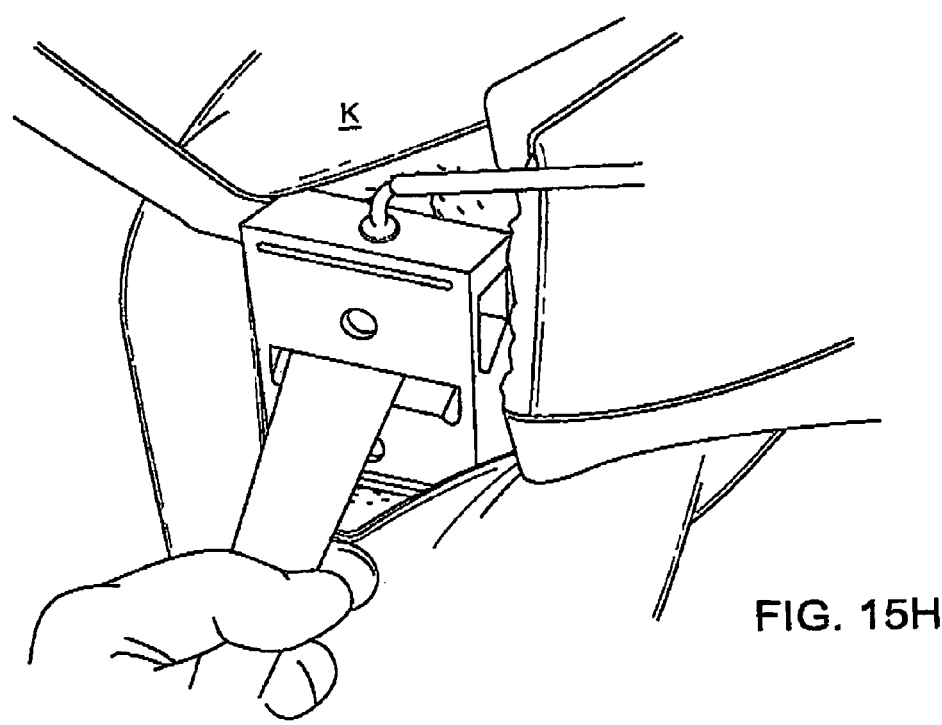
Figure 15I:
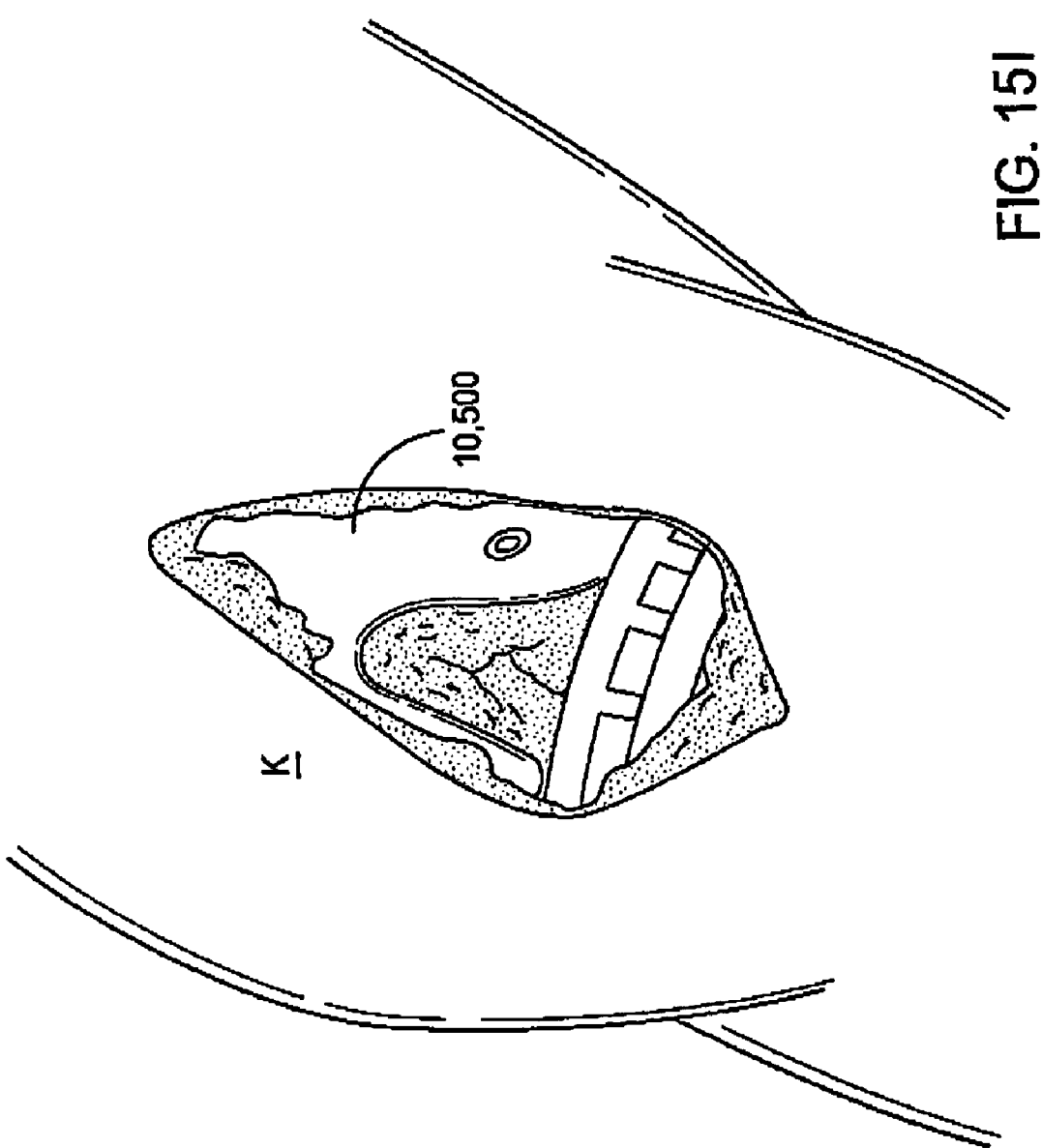
Figure 15J:
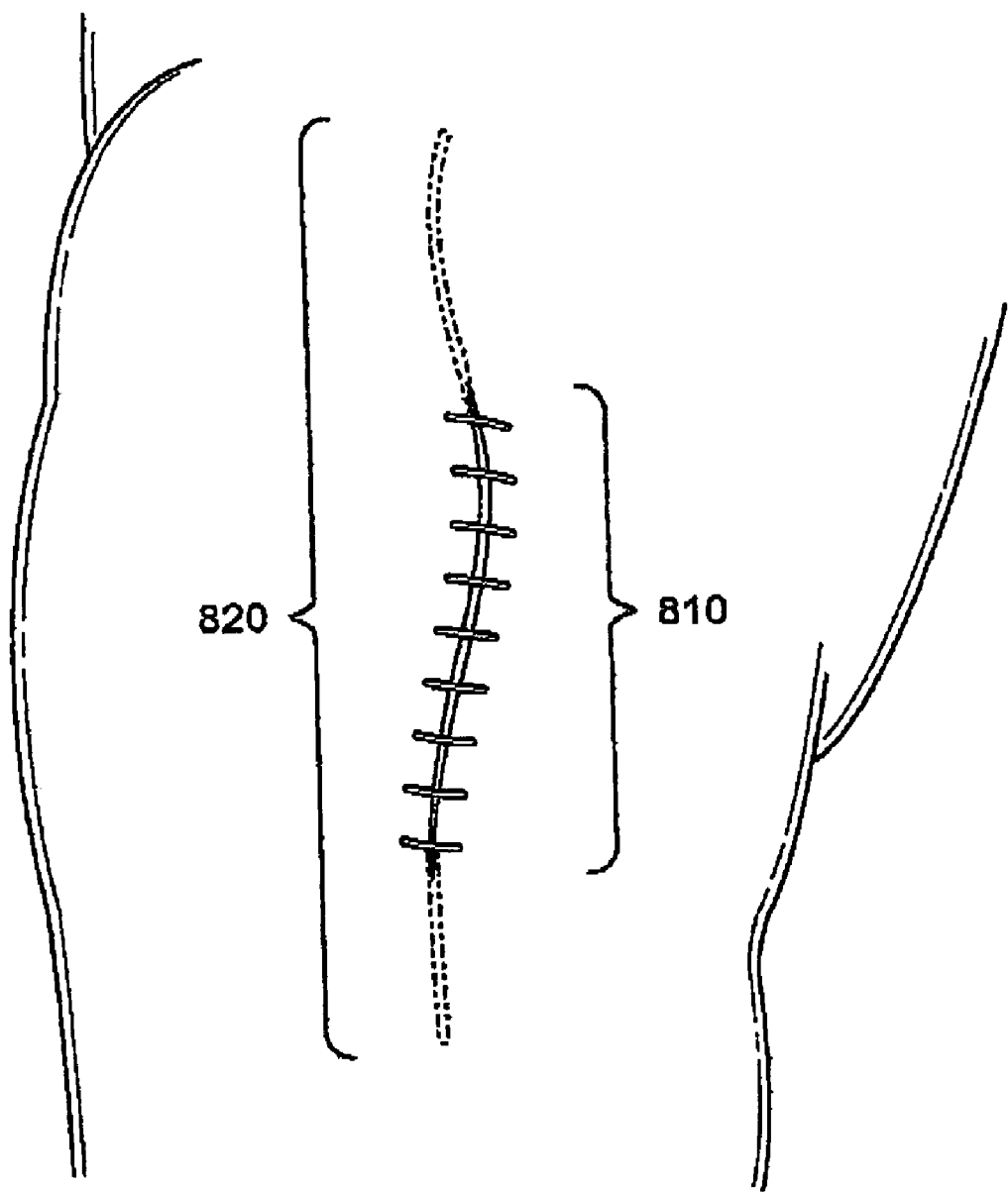

Once a desired gap/balance has been obtained, then a drilling step 760 can be performed as shown in FIG. 15E, wherein the positioning features of system 10/device 500, such as apertures 502 are used as guides to drill holes in the distal femur for placement of a cutting guide described herein. The balancing system is then removed and a cutting guide is then placed over the distal femur using the drilled holes as guides in a cutting guide placement step 770 (See FIG. 15F). Then the cutting guide is used to make final cuts to the femur in cutting step 780 as shown in FIGS. 15G-15H. These final cuts are used to determine the position and orientation of a final femoral prosthetic component to be implanted in the knee (this can include all or a portion of the components of system 10). Such cuts will typically include anterior and posterior chamfer cuts (see FIGS. 15G-15H) to help secure the femoral prosthetic solidly in place. Then the cutting guide is removed a knee final prosthetic device is attached and implanted in an attachment/implant step 790 shown in FIG. 15I. The incision is then sown up in a closing step 800 shown in FIG. 15J. As FIG. 15J shows, the minimally invasive method using system 10/device 500 results in a much smaller incision 810 vs. the incision 820 from a traditional knee implant procedure.

It is contemplated that any of the devices, systems and methods described above may be incorporated with any suitable knee surgery procedures or systems currently used or discovered in the future. For example, inventive devices, systems and methods may be readily incorporated with any number of different visualization, navigation and/or robotic systems for performing a knee surgery, such as image-guided systems for performing, planning or enhancing a TKA procedure, robotic surgery systems such as the da Vinci® Surgical System provided by Intuitive Surgical, Inc. (Sunnyvale, Calif.), or the like. Any suitable imaging or visualization modality and technique may be used with various embodiments of the devices, systems and methods of the invention, including but not limited to arthroscopic, infrared or ultrasound imaging.

The foregoing description of various embodiments of the invention has been presented for purposes of illustration and description. It is not intended to limit the invention to the precise forms disclosed. Many modifications, variations and refinements will be apparent to practitioners skilled in the art. Further, elements or acts from one embodiment can be readily recombined with one or more elements or acts from other embodiments. Also, elements or acts from one embodiment can be readily substituted with elements or acts of another embodiment to form new embodiments. Moreover elements that are shown or described as being combined with other elements, can in various embodiments, exists as stand alone elements. Hence, the scope of the present invention is not limited to the specifics of the exemplary embodiments, but is instead limited solely by the appended claims.

What is claimed is:

1. A device for performing a minimally invasive procedure on a knee, the device comprising a femoral assembly engageable with a distal femur, the femoral assembly comprising:

a stationary femoral member removably attachable to a distal femur;

an adjustable femoral member movably coupled with the stationary member to adjust tension in at least one ligament of or adjacent the knee, the adjustable femoral member including a medial portion and a lateral portion and at least one positioning feature that moves relative to the distal femur as the adjustable femoral member is adjusted and thus identifies at least one position on the distal femur for facilitating completion of the surgical procedure to enhance at least one of range of motion, stability or patella tracking of the knee, wherein the adjustable femoral member is configured to be movably couplable with a tibial member engaged with a proximal tibia to allow the knee to be moved through a range of motion without removing the femoral and tibial members; and an adjustment mechanism coupled to the femoral assembly, the mechanism including an actuator, the actuator positioned proximate the medial or the lateral portion of the adjustable femoral member, the actuator configured to adjust an opposite portion of the adjustable member to adjust tension in the at least one ligament, wherein the stationary member and the adjustable member are pivotally coupled.

2. The device of claim 1, wherein the actuator is positioned proximate the medial portion of the adjustable member and the adjustment mechanism is configured to adjust the lateral portion of the adjustable member.

3. The device of claim 1, wherein the stationary femoral member is engageable with a cut surface at the distal end of the distal femur.

4. The device of claim 3, wherein the stationary femoral member has a cross sectional shape configured to correlate to a cross sectional shape of the cut surface of the distal femur.

5. The device of claim 1, further comprising a stop coupled to the femoral assembly, the stop configured to limit movement of the adjustable femoral member.

6. The device of claim 1, wherein the stationary femoral member includes at least one access opening aligned with the at least one positioning feature, the access opening configured to allow direct access to the femur through the positioning feature independent of a position of the adjustable femoral member relative to the stationary member.

7. The device of claim 6, wherein the at least one access opening includes a first opening aligned with a first positioning feature and a second opening aligned with a second positioning feature, wherein the openings provide access to the femur though both positioning features throughout a range of motion of the adjustable femoral member relative to the stationary member.

8. The device of claim 1, wherein the mechanism rotably adjusts the adjustable femoral member relative to the pivotally coupled stationary femoral member.

9. The device of claim 1, further comprising at least one pivotal coupling coupled to the adjustable member.

10. The device of claim 9, wherein the pivotal coupling is positioned to have a medial or lateral portion of the adjustable member rotate relative to an opposite portion of the adjustable member.

11. The device of claim 1, further comprising a stop coupled to the femoral assembly, the stop configured to limit pivotal movement of the adjustable femoral member.

12. The device of claim 1, wherein the adjustable femoral member is configured to be slidably coupled with the tibial member.

13. The device of claim 1, wherein the adjustable femoral member is configured to be movably coupled to the tibial member via the application of force from the at least one ligament.

14. The device of claim 1, wherein the femoral assembly has a shape configured to allow determination of a desired position of the adjustable femoral member relative to the tibial member throughout the range of motion of the knee.

15. The device of claim 1, wherein the actuator is configured to be actuated throughout the range of motion of the knee.

16. The device of claim 1, wherein the actuator is configured to be actuated throughout the range of motion of the knee without physical or visual obstruction of a surgical field of the knee.

17. The device of claim 1, wherein the actuator comprise a screw.

18. The device of claim 1, wherein the actuator is configured to be engaged by an adjustment device.

19. The device of claim 18, wherein the adjustment device is a hand-held tool or a wrench.

20. The device of claim 18, wherein the adjustment device has a shape and size configured to engage the actuator throughout the range of motion of the knee.

21. The device of claim 1, wherein the adjustment mechanism comprises at least one of a screw, pin, spring, lever, rod, bushing or guide.

22. The device of claim 1, wherein the adjustment mechanism is coupled to the adjustable femoral member.

23. The device of claim 1, wherein the adjustment mechanism is configured to allow adjustment of the adjustable member to a desired location throughout the range of motion of the knee without eversion of a patella.

24. The device of claim 1, wherein the adjustable femoral member comprises:
   at least one distal femoral portion for emulating a distal surface of the femur; and
   at least one posterior condylar portion to emulate posterior condylar surfaces of the femur.

25. The device of claim 24, wherein the posterior condylar portion comprises:
   a medial femoral posterior condylar portion; and
   a lateral femoral posterior condylar portion.

26. The device of claim 25, wherein the distal femoral portion, the medial femoral posterior condylar portion, and the lateral femoral posterior condylar portion all comprise a single integral structure.

27. The device of claim 1, wherein the stationary femoral member comprises:
   at least one distal femoral plate for coupling the distal femoral portion of the adjustable femoral member to the distal femur; and
   at least one posterior condylar member extending from the distal femoral portion to contact at least part of a medial posterior femoral condyle and a lateral posterior femoral condyle of the distal femur.

28. The device of claim 27, wherein the at least one posterior condylar member comprises:
   a medial femoral posterior condylar member; and
   a lateral femoral posterior condylar member.

29. The device of claim 28, wherein the distal femoral plate, the medial femoral posterior condylar member, and the lateral femoral posterior condylar member all comprise one piece or extrusion.

30. The device of claim 28, wherein the medial femoral posterior condylar portion of the adjustable femoral member is adjustable relative to the medial femoral posterior condylar member of the stationary femoral member, and wherein the lateral femoral posterior condylar portion of the adjustable femoral member is separately adjustable relative to the lateral femoral posterior condylar member of the stationary femoral member.

31. The device of claim 24, wherein the at least one posterior condylar portion of the adjustable femoral member is movably couplable with one or more complementary depressions in the tibial member.

32. The device of claim 31, wherein the at least one posterior condylar member comprises:
   a medial femoral posterior condylar member slidably couplable with a medial depression of the tibial member; and
   a lateral femoral posterior condylar member slidably couplable with a lateral depression of the tibial member.

33. The device of claim 1, wherein the at least one positioning feature of the adjustable femoral member is selected from the group consisting of an aperture, a drill bit guide, a surface marker, a surface feature, a measurement device, an embedded marker, a fiducial, a transponder, a transceiver and a sensor.

34. The device of claim 33, wherein the at least one positioning feature facilitates at least one of placing a cutting guide on the distal femur for making bone cuts, making one or more bone cuts on the distal femur, and positioning a prosthetic femoral component on the distal femur.

35. The device of claim 33, wherein the at least one positioning feature comprises at least two apertures.

36. The device of claim 35, wherein each of the at least two apertures is configured to guide a drill bit to form a hole in the distal femur for attaching a cutting guide to the femur.

37. The device of claim 35, wherein each of the at least two apertures are configured to receive at least one of a marker, a fiducial, a transponder, a transceiver and a sensor.

38. The device of claim 35, wherein the at least two apertures extend through the adjustable femoral member and through apertures in the stationary femoral member to the distal femur.

39. The device of claim 38, wherein the at least two apertures are positioned asymmetrically on the adjustable femoral member to provide for a built-in desired flexibility in the ligaments when the surgical procedure is completed.

40. The device of claim 33, wherein at least one of the adjustable femoral member and the positioning feature(s) is asymmetrically oriented relative to the stationary member to provide built-in enhanced range of motion when the surgical procedure is completed.

41. The device of claim 40, further comprising multiple adjustable femoral members, each having a different asymmetry relative to the stationary member, wherein one of the multiple adjustable femoral members is selected for facilitating the surgical procedure to provide a desired range of motion when the surgical procedure is completed.

42. The device of claim 1, wherein the tibial member is engageable with a cut surface of the proximal tibia.

43. The device of claim 42, wherein the at least one tibial member comprises at least one of a shim, paddle, plate, bar, platform or rod.

44. The device of claim 43, wherein the at least one tibial member comprises a plurality of tibial shims having different thicknesses or heights, wherein any one of the plurality of shims may be selected for engaging with the cut surface of the proximal tibia to provide a desired amount of tension in the ligaments.

45. The device of claim 44, wherein the at least one tibial member further comprises a plate for removably attaching to the cut surface of the proximal tibia, disposed between the cut surface and the selected tibial shim.

46. The device of claim 1, wherein the femoral member and the tibial member are movably coupled via force provided by the at least one ligament of or adjacent the knee.

47. The device of claim 1, wherein the femoral and tibial members, when engaged with the distal femur and proximal tibia respectively, are disposed primarily within a joint space between the distal femur and the proximal tibia.

48. The device of claim 47, wherein a patella of the knee remains approximately in its anatomical position while the femoral and tibial members are engaged and the knee is moved through the range of motion.

49. The device of claim 1, wherein the movable coupling of the femoral and tibial members allows for flexion and extension through the range of motion.

50. The device of claim 49, wherein the range of motion comprises a range from approximately full extension of the knee to approximately full flexion of the knee.

51. The device of claim 1, wherein the stationary femoral member comprises at least one material selected from the group consisting of plastics, thermoplastics, carbon fiber composite, polymer composite, aluminum, stainless steel, metal composite, cobalt-chrome alloys or titanium.

52. The device of claim 1, wherein the adjustable femoral member comprises at least one material selected from the group consisting of plastics, thermoplastics, carbon fiber composite, polymer composite, aluminum, stainless steel, metal composite, cobalt-chrome alloys or titanium.

53. The device of claim 1, further comprising at least one grasping member coupled with at least one of the stationary and adjustable femoral members for facilitating placement and/or removal of the device from the knee.

54. A device for performing a minimally invasive procedure on a knee, the device comprising a femoral assembly, the femoral assembly comprising:

a stationary femoral member for removably attachable to a distal femur; and an adjustable femoral member movably coupled with the stationary member to adjust tension in at least one ligament of or adjacent the knee, the adjustable femoral member comprising a medial portion and lateral portion and at least one positioning feature that moves relative to the distal femur as the adjustable femoral member is adjusted and thus identifies at least one position on the distal femur for facilitating completion of the surgical procedure to enhance at least one of range of motion, stability or patella tracking of the knee; and a self adjustment mechanism coupled to the femoral assembly, the adjustment means configured to adjust the adjustable femoral member responsive to a tension of the at least one ligament;

wherein the adjustable femoral member is configured to be movably couplable with a tibial member engaged with a proximal tibia to allow the knee to be moved through a range of motion without removing the femoral and tibial members and wherein the self-adjustment mechanism comprises a plurality of pre-adjusted femoral members, each having a different asymmetry relative to the stationary member, wherein one of the pre-adjusted members is selected to provide a desired range of motion when the surgical procedure is completed.

55. The device of claim 54, wherein the self adjustment mechanism comprises at least one of a spring, a leaf spring, a coil spring, a flat spring, a clock spring, a shape memory material or a shape memory member.

56. The device of claim 54, wherein the self adjustment mechanism is disposed between the stationary and the adjustable femoral member.

57. The device of claim 54, wherein the self adjustment mechanism is disposed on or within the adjustable femoral member.

58. The device of claim 54, wherein the self adjustment mechanism is configured to put the at least one tendon into tension.

59. The device of claim 54, wherein the self adjustment mechanism has a spring force configured to put the at least one tendon into tension to balance the knee through the range of motion.

60. The device of claim 54, wherein the self adjustment mechanism adjusts relative to the stationary femoral member to adjust tension in at least one of a medial collateral ligament and a lateral collateral ligament of the knee.

* * * * *